(12) United States Patent
Sakai et al.

(10) Patent No.: US 11,980,419 B2
(45) Date of Patent: May 14, 2024

(54) OPTICAL COHERENCE TOMOGRAPHY APPARATUS, CONTROL METHOD OF THE SAME, OPTICAL MEASUREMENT METHOD, AND RECORDING MEDIUM

(71) Applicant: TOPCON CORPORATION, Tokyo (JP)

(72) Inventors: Jun Sakai, Kuki (JP); Toshihiro Mino, Warabi (JP)

(73) Assignee: TOPCON CORPORATION, Tokyo (JP)

( * ) Notice: Subject to any disclaimer, the term of this patent is extended or adjusted under 35 U.S.C. 154(b) by 760 days.

(21) Appl. No.: 16/925,346

(22) Filed: Jul. 10, 2020

(65) Prior Publication Data

US 2021/0007600 A1 Jan. 14, 2021

(30) Foreign Application Priority Data

Jul. 11, 2019 (JP) ................ 2019-129023

(51) Int. Cl.
*A61B 3/10* (2006.01)
*A61B 3/00* (2006.01)
*A61B 3/12* (2006.01)

(52) U.S. Cl.
CPC ............ *A61B 3/102* (2013.01); *A61B 3/0025* (2013.01); *A61B 3/1233* (2013.01)

(58) Field of Classification Search
CPC ..... A61B 3/102; A61B 3/0025; A61B 3/1233; A61B 3/12; A61B 3/1241; A61B 3/135; A61B 3/14
See application file for complete search history.

(56) References Cited

U.S. PATENT DOCUMENTS

2007/0002277 A1\* 1/2007 Hanebuchi ............ A61B 3/102
351/206
2007/0276269 A1 11/2007 Yun et al.
(Continued)

FOREIGN PATENT DOCUMENTS

JP 2009-536740 A 10/2009
JP 2013-184018 A 9/2013
(Continued)

OTHER PUBLICATIONS

Japanese Office Action dated Jan. 31, 2023 in corresponding Japanese Patent Application No. 2019-129023 (with machine-generated English translation), 6 pages.
(Continued)

*Primary Examiner* — Sean D Mattson
(74) *Attorney, Agent, or Firm* — XSENSUS LLP

(57) ABSTRACT

An exemplary OCT apparatus includes a scanner, controller, phase information generator, phase information processor. The scanner applies an OCT scan to an object using an optical scanner. The controller controls the scanner to perform a first scan that scans a cross section of the object in a first scan direction and a second scan that scans a cross section of the object in a second scan direction opposite to the first scan direction. The phase information generator generates first phase information based on first acquisition data acquired by the first scan and second phase information based on second acquisition data acquired by the second scan. The phase information processor generates composite phase information based on the first phase information and the second phase information.

20 Claims, 20 Drawing Sheets

(56) References Cited

U.S. PATENT DOCUMENTS

| | | | |
|---|---|---|---|
| 2012/0316434 A1 | 12/2012 | Yun et al. | |
| 2013/0148182 A1 | 6/2013 | Yu et al. | |
| 2015/0092195 A1* | 4/2015 | Blatter | A61B 5/0261 |
| | | | 356/479 |
| 2015/0313466 A1* | 11/2015 | Yoshida | A61B 5/026 |
| | | | 600/425 |
| 2016/0150954 A1 | 6/2016 | Furuuchi et al. | |
| 2016/0302738 A1 | 10/2016 | Yoshida et al. | |
| 2016/0310024 A1 | 10/2016 | Yoshida et al. | |
| 2016/0367132 A1 | 12/2016 | Yun et al. | |
| 2018/0149464 A1* | 5/2018 | Jochinsen | G01B 9/02044 |
| 2018/0160901 A1* | 6/2018 | Guo | A61B 3/102 |

FOREIGN PATENT DOCUMENTS

| | | | | |
|---|---|---|---|---|
| JP | 2014-068703 A | | 4/2014 | |
| JP | 2017-46924 A | | 3/2017 | |
| JP | 2017-101973 A | | 6/2017 | |
| JP | 2017-104217 A | | 6/2017 | |
| JP | 2017-144232 A | | 8/2017 | |
| JP | 2018-121888 A | | 8/2018 | |
| JP | 2018121888 A | * | 8/2018 | ........... A61B 3/0008 |

OTHER PUBLICATIONS

Chinese Office Action issued Mar. 6, 2024, in corresponding Chinese Patent Application 202010640964.8, 20 pp.

* cited by examiner

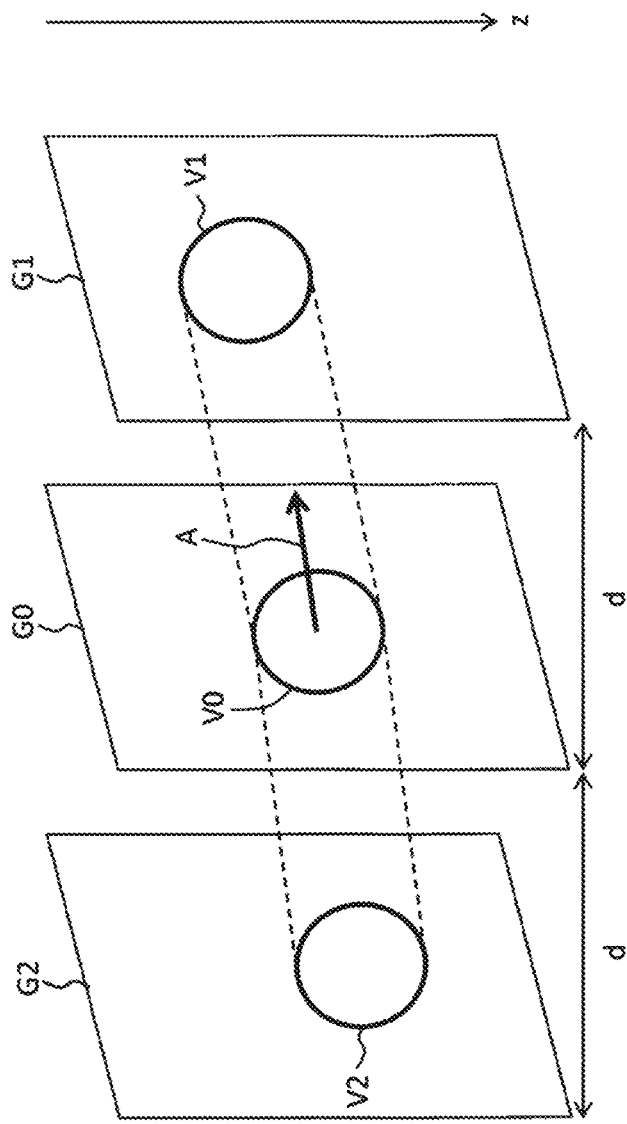

OPTICAL COHERENCE TOMOGRAPHY APPARATUS, CONTROL METHOD OF THE SAME, OPTICAL MEASUREMENT METHOD, AND RECORDING MEDIUM

CROSS-REFERENCE TO RELATED APPLICATION

This application is based upon and claims the benefit of priority from Japanese Patent Application No. 2019-129023, filed Jul. 11, 2019; the entire contents of which are incorporated herein by reference.

FIELD

The present disclosure relates generally to an optical coherence tomography (OCT) technique, and in particular to an OCT apparatus, a control method of the same, an optical measurement method, and a recording medium.

BACKGROUND

OCT is typically a technique for imaging a light-scattering medium with a resolution of a micrometer level using low-coherence light, and has been put to practical use in fields such as biology and medicine. In these fields, OCT has been applied not only to imaging the morphology and structure of an object, but also to imaging the movement of fluid and imaging the optical characteristics of fluid. Examples thereof include an OCT blood flow meter and a polarization sensitive OCT apparatus.

OCT blood flow meters and polarization sensitive OCT apparatuses use phase information of acquired data. An image based on phase information is referred to as a phase image or the like.

These techniques are disclosed, for example, in the following documents: Japanese Unexamined Patent Application Publication (Translation of PCT Application) No. 2009-536740 (US Patent Application Publication Nos. 2007/276269 A1, 2012/316434 A1, and 2016/367132 A1); Japanese Unexamined Patent Application Publication No. 2013-184018 (US Patent Application Publication Nos. 2015/313466 A1, 2016/302738 A1, and 2016/310024 A1); and Japanese Unexamined Patent Application Publication No. 2017-101973.

The OCT scan is realized using an optical deflector (optical scanner) such as a galvanometer mirror or a MEMS mirror. A typical optical scanner includes a reflecting mirror that rotates about an axis (see FIGS. 1A and 1B). When incident light is reflected at a position off the rotation axis of the reflecting mirror like shown in FIG. 1B, the path length of the light changes as the reflecting mirror rotates, and thus changes occur in the phase information. As a result, for example, with an OCT blood flow meter, the position of the reference point (zero point) of the blood flow velocity is shifted and an error occurs in the measurement result.

Note that this problem can be solved when incident light is guided toward the rotation axis of the reflecting mirror, as shown in FIG. 1A, and therefore the incident light is reflected at the fixed position of the reflecting surface. However, in order to achieve this, not only an extremely highly precise optical arrangement is required, but also a deviation of and an error in the optical arrangement on account of environmental conditions (e.g., temperature, humidity, etc.) must be dealt with. Considering these circumstances, it can be said that it is difficult to achieve a preferable configuration that guides the incident light toward the rotation axis of the reflecting mirror.

In addition, an optical scanner for general OCT apparatuses includes two reflecting mirrors with different deflection directions arranged in series in order to enable three dimensional scanning. In other words, incident light is deflected by a first reflecting mirror and then by a second reflecting mirror. Therefore, the position on the second reflecting mirror onto which the incident light is projected depends on the orientation of the first reflecting mirror. This means that, even if the incident light may be guided toward the rotation axis of the first reflecting mirror, the incident position on the second reflecting mirror will not be constant, and eventually the problem mentioned above will arise.

SUMMARY

An object of the present disclosure is to eliminate errors in phase information caused by optical scanners.

The first exemplary aspect is an optical coherence tomography (OCT) apparatus comprising: a scanner configured to apply an OCT scan to an object using an optical scanner; a controller configured to control the scanner to perform at least one first scan that scans a cross section of the object in a first scan direction and at least one second scan that scans a cross section of the object in a second scan direction opposite to the first scan direction; a phase information generator configured to generate at least one piece of first phase information based on at least one piece of first acquisition data acquired by the at least one first scan and at least one piece of second phase information based on at least one piece of second acquisition data acquired by the at least one second scan; and a phase information processor configured to generate composite phase information based on the at least one piece of first phase information and the at least one piece of second phase information.

The second exemplary aspect is the OCT apparatus of the first exemplary aspect, wherein the controller is configured to control the scanner to perform one or more first scans and one or more second scans in an alternate manner.

The third exemplary aspect is the OCT apparatus of the second exemplary aspect, wherein the controller is configured to control the scanner to perform a single first scan and a single second scan in an alternate manner.

The fourth exemplary aspect is the OCT apparatus of the third exemplary aspect, wherein the controller is configured to control the scanner to apply the single first scan and the single second scan in an alternate manner to a same cross section.

The fifth exemplary aspect is the OCT apparatus of the third or fourth exemplary aspect, wherein the phase information processor is configured to generate composite phase information based on first phase information corresponding to a first scan and second phase information corresponding to a second scan performed immediately before or immediately after the first scan.

The sixth exemplary aspect is the OCT apparatus of any of the first to fourth exemplary aspects, wherein the phase information processor is configured to generate composite phase information based on first phase information corresponding to a first scan and second phase information corresponding to a second scan where a time lag between the first scan and the second scan is not exceeding a predetermined threshold.

The seventh exemplary aspect is the OCT apparatus of any of the first to fourth exemplary aspects, wherein the phase information represents a substantially periodic change of the object, and the phase information processor is configured to generate composite phase information based on first phase information corresponding to a first scan performed at a time phase of the change and second phase information corresponding to a second scan performed at a time phase substantially the same as the time phase for the first scan.

The eighth exemplary aspect is the OCT apparatus of any of the first to seventh exemplary aspects, wherein the phase information processor is configured to generate composite phase information by averaging first phase information and second phase information.

The ninth exemplary aspect is the OCT apparatus of any of the first to eighth exemplary aspects, wherein the optical scanner includes a reflecting mirror rotatable in a reciprocating manner, and the controller is configured to control the scanner to acquire data while the reflecting mirror is rotating at substantially a constant speed.

The tenth exemplary aspect is the OCT apparatus of any of the first to ninth exemplary aspects, wherein the phase information generator includes a phase image construction unit configured to construct a phase image that represents a temporal change in a phase difference, and the phase information processor is configured to generate composite phase information based on at least one first phase image corresponding to the at least one first scan and at least one second phase image corresponding to the at least one second scan.

The eleventh exemplary aspect is the OCT apparatus of any of the first to tenth exemplary aspects, wherein the controller is configured to control the scanner to repeatedly perform each of the first scan and the second scan, the phase information generator is configured to generate a plurality of pieces of first phase information based on a plurality of pieces of first acquisition data acquired by a plurality of first scans, and to generate a plurality of pieces of second phase information based on a plurality of pieces of second acquisition data acquired by a plurality of second scans, and the phase information processor is configured to generate a plurality of phase information groups each of which includes both one or more pieces of first phase information and one or more pieces of second phase information based on the plurality of pieces of first phase information and the plurality of pieces of second phase information, and to generate a plurality of pieces of composite phase information based respectively on the plurality of phase information groups.

The twelfth exemplary aspect is the OCT apparatus of any of the eleventh exemplary aspects, wherein the object is a living body, and the OCT apparatus further comprising a blood flow information generator configured to generate blood flow information representing hemodynamics of the living body based on the plurality of pieces of composite phase information generated from the plurality of phase information groups by the phase information processor.

The thirteenth exemplary aspect is a method of controlling an OCT apparatus that includes a processor and a scanner configured to apply an OCT scan to an object using an optical scanner, the method comprising: controlling the scanner to perform at least one first scan that scans a cross section of the object in a first scan direction; controlling the scanner to perform at least one second scan that scans a cross section of the object in a second scan direction opposite to the first scan direction; controlling the processor to generate at least one piece of first phase information based on at least one piece of first acquisition data acquired by the at least one first scan; controlling the processor to generate at least one piece of second phase information based on at least one piece of second acquisition data acquired by the at least one second scan; and controlling the processor to generate composite phase information based on the at least one piece of first phase information and the at least one piece of second phase information. Any step or process corresponding to the OCT apparatus according to any of the above exemplary aspects may be combined with the controlling method according to the thirteenth exemplary aspect.

The fourteenth exemplary aspect is a program configured to cause a computer to execute the method of controlling the OCT apparatus of the thirteenth exemplary aspect. Any configuration corresponding to the OCT apparatus according to any of the above exemplary aspects may be combined with the program according to the fourteenth exemplary aspect.

The fifteenth exemplary aspect is an optical measurement method for acquiring data by applying an OCT scan to an object using an optical scanner, the method comprising: performing at least one first scan that scans a cross section of the object in a first scan direction; performing at least one second scan that scans a cross section of the object in a second scan direction opposite to the first scan direction; generating at least one piece of first phase information based on at least one piece of first acquisition data acquired by the at least one first scan; generating at least one piece of second phase information based on at least one piece of second acquisition data acquired by the at least one second scan; and generating composite phase information based on the at least one piece of first phase information and the at least one piece of second phase information. Any step or process corresponding to the OCT apparatus according to any of the above exemplary aspects may be combined with the optical measurement method according to the thirteenth exemplary aspect.

The sixteenth exemplary aspect is a program configured to cause an OCT apparatus to execute the optical measurement method of the fifteenth exemplary aspect. Any configuration corresponding to the OCT apparatus according to any of the above exemplary aspects may be combined with the program according to the sixteenth exemplary aspect.

The seventeenth exemplary aspect is a computer-readable non-transitory recording medium storing the program of the fourteenth or sixteenth exemplary aspect. Any configuration corresponding to the OCT apparatus according to any of the above exemplary aspects may be combined with the recording medium according to the seventeenth exemplary aspect.

According to some exemplary aspects, errors in phase information caused by optical scanners can be eliminated.

BRIEF DESCRIPTION OF THE DRAWINGS

FIG. 8A is a schematic diagram for describing an example of the operation of the blood flow measurement apparatus (optical coherence tomography apparatus) of an exemplary aspect according to the embodiment.

DETAILED DESCRIPTION

Figure 1A:
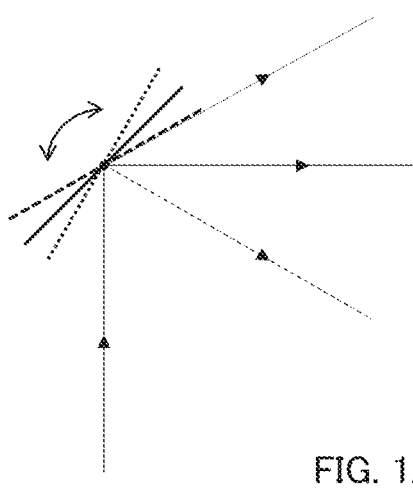
FIG. 1A is a schematic diagram for describing an error in phase information caused by an optical scanner for OCT scanning.

Optical coherence tomography (OCT) apparatuses, control methods of the same, optical measurement methods, programs, and recording mediums according to some embodiments will be described in detail while referring to the drawings. An optical coherence tomography apparatus is configured to apply OCT to an object to acquire data and generate at least phase information from the acquired data. Furthermore, the optical coherence tomography apparatus may be configured to be capable of generating intensity information (amplitude information) from the acquired data. Any of the contents of the documents cited in the present specification and any other known techniques may be incorporated into some embodiments.

The following exemplary embodiments disclose blood flow measurement apparatuses having OCT functions. In the exemplary embodiments, Fourier domain OCT (e.g., swept source OCT) is adopted as their OCT systems, and living eyes (e.g., eye fundi) are adopted as the objects to be measured. However, adoptable OCT systems are not limited to swept source OCT. For example, spectral domain OCT, time domain OCT, polarization sensitivity OCT, phase sensitivity OCT, or other OCT systems may be adopted. Further, the blood flow measurement apparatuses according to the exemplary embodiments are configured as multifunctional apparatuses that are a combination of an OCT apparatus and a fundus camera; however, apparatus configurations for fundus blood flow measurement is not limited to this, and some blood flow measurement apparatuses may be configured as a combination of an OCT apparatus and any kind of fundus imaging apparatus other than a fundus camera. Examples of such a fundus imaging apparatus include a scanning laser ophthalmoscope (SLO), a slit lamp microscope, and an ophthalmic surgical microscope, which are used at least for fundus observation. When fundus observation can be realized by using live OCT functions, blood flow measurement apparatuses according to some exemplary embodiments may not include such an fundus imaging apparatus. Similar configurations may be applied when the site subjected to be measured is other than the fundus.

<Configuration of Blood Flow Measurement Apparatus of Exemplary Embodiments>

Figure 2:
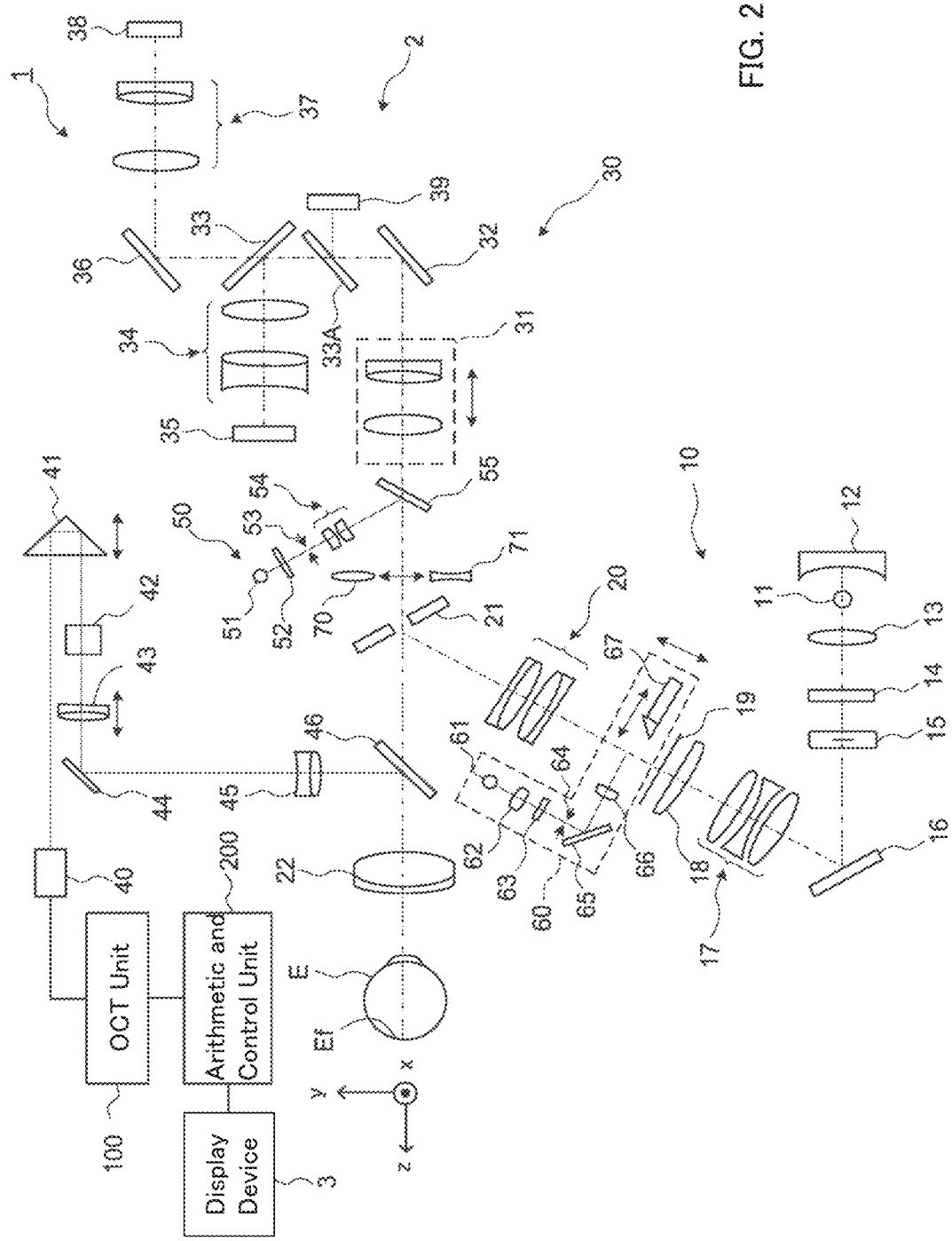
FIG. 2 is a schematic diagram showing an example of the configuration of the blood flow measurement apparatus (optical coherence tomography apparatus) of an exemplary aspect according to the embodiment.

As shown in FIG. 2, the blood flow measurement apparatus 1 includes the fundus camera unit 2, the OCT unit 100 and the arithmetic and control unit 200. The fundus camera unit 2 is provided with an optical system and mechanisms for acquiring front images of the subject's eye. The OCT unit 100 includes part of an optical system and part of mechanisms for applying OCT scans to the subject's eye. Another part of the optical system and another part of the mechanisms for applying OCT scans to the subject's eye are provided in the fundus camera unit 2. The arithmetic and control unit 200 includes one or more processors configured and programmed to execute various calculations and controls. In addition, the blood flow measurement apparatus 1 may also include any elements or units such as a member for supporting the face of the subject (e.g., a chin rest, a forehead rest) and a lens unit for switching the sites subjected to OCT measurement (e.g., an attachment for an anterior eye segment OCT).

In the present specification, the term "processor" is used to mean, for example, a circuit such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or the like. The processor realizes the functions according to the embodiment, for example, by reading out and executing a program stored in a storage circuit or a storage device.

<Fundus Camera Unit 2>

The fundus camera unit 2 is provided with an optical system for photographing the fundus Ef of the subject's eye E. Images of the fundus Ef (referred to as fundus images, fundus photographs, or the like) obtained include front images such as observation images and photographed images. An observation image is obtained by capturing a moving image using near-infrared light. A photographed image is a still image obtained by using flash light.

The fundus camera unit 2 includes the illumination optical system 10 and the photographing optical system 30. The illumination optical system 10 projects illumination light onto the subject's eye E. The photographing optical system 30 detects the return light of the illumination light from the subject's eye E. The measurement light incident from the OCT unit 100 is directed to the subject's eye E through the optical path in the fundus camera unit 2, and the return light thereof is directed to the OCT unit 100 through the same optical path.

The light output from the observation light source 11 of the illumination optical system 10 (called observation illumination light) is reflected by the concave mirror 12, passes through the condenser lens 13, and becomes near-infrared light after passing through the visible cut filter 14. Further, the observation illumination light is once converged at a location near the photographing light source 15, reflected by the mirror 16, and passes through the relay lens system 17, the relay lens 18, the diaphragm 19, and the relay lens system 20. Then, the observation illumination light is reflected on the peripheral part (i.e., the surrounding area of the aperture part) of the aperture mirror 21, penetrates the dichroic mirror 46, and refracted by the objective lens 22, thereby illuminating the subject's eye E (the fundus Ef thereof). The return light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Furthermore, the return light passes through the half mirror 33A, is reflected by the dichroic mirror 33, and forms an image on the light receiving surface of the image sensor 35 by the condenser lens 34. The image sensor 35 detects the return light at a predetermined frame rate. Note that the focus of the photographing optical system 30 is adjusted to coincide with the fundus Ef or the anterior eye segment.

The light output from the photographing light source 15 (called photographing illumination light) passes through the same route as that of the observation illumination light and is projected onto the fundus Ef. The return light of the photographing illumination light from the subject's eye E passes through the same route as that of the return light of the observation illumination light, is guided to the dichroic mirror 33, passes through the dichroic mirror 33, is reflected by the mirror 36, and forms an image on the light receiving surface of the image sensor 38 by the condenser lens 37.

The liquid crystal display (LCD) 39 displays a fixation target (fixation target image). Part of the light beam output from the LCD 39 is reflected by the half mirror 33A, reflected by the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef.

By changing the display position of the fixation target image on the screen of the LCD 39, the fixation position of the subject's eye E by the fixation target can be changed. Examples of the fixation position includes the followings: a fixation position for acquiring an image centered on the macula; a fixation position for acquiring an image centered on the optic nerve head; a fixation position for acquiring an image centered on the fundus center that is located between the macula and the optic nerve head; and a fixation position for acquiring an image of a site far away from the macula (periphery of the fundus). A user interface such as a graphical user interface (GUI) for designating at least one of such typical fixation positions can be provided. Further, a user interface such as a GUI for manually changing the fixation position (i.e., the display position of the fixation target) can be provided.

The configuration for presenting the fixation target, capable of changing the fixation position, to the subject's eye E is not limited to display devices such as an LCD. For example, a fixation matrix device can be adopted in place of a display device. The fixation matrix device includes a plurality of light emitting parts (e.g., light emitting diodes) that are disposed in a matrix-like arrangement (in a matrix array). In this case, the fixation position of the subject's eye E by the fixation target can be changed by lighting one (or more) of the plurality of light emitting parts in a selective manner. As another example, the fixation target usable for fixation position change may be generated by employing one or more movable light emitting parts.

The alignment optical system 50 generates an alignment indicator used for the alignment of the optical system with respect to the subject's eye E. The alignment light output from the light emitting diode (LED) 51 travels through the diaphragm 52, the diaphragm 53, and the relay lens 54, is reflected by the dichroic mirror 55, passes through the aperture part of the aperture mirror 21, penetrates the dichroic mirror 46, and is projected onto the subject's eye E via the objective lens 22. The return light of the alignment light from the subject's eye E (e.g., the cornea reflection light) passes through the same route as that of the return light of the observation illumination light and is guided to the image sensor 35. Based on the received image, manual alignment and/or automatic alignment can be performed. The received image is referred to as an alignment indicator image.

As in a conventional case, the alignment indicator image of the present example includes two bright spot images whose positions change according to the alignment state. When the relative position between the subject's eye E and the optical system changes in the xy direction, the two bright spot images are shifted in the xy direction in an integrated manner. When the relative position between the subject's eye E and the optical system changes in the z direction, the relative position (distance) between the two bright spot images changes. When the distance between the subject's eye E and the optical system in the z direction matches a working distance set in advance, the two bright spot images overlap with each other. When the position of the subject's eye E matches the position of the optical system in the xy direction, the two bright spot images are presented within or near a given alignment target. When the distance between the subject's eye E and the optical system in the z direction matches the working distance, and the position of the subject's eye E matches the position of the optical system in the xy direction, the two bright spot images overlap with each other and are presented within the alignment target.

For the automatic alignment, the data processor 230 detects the positions of the two bright spot images, and the main controller 211 controls the movement mechanism 150 (described later) on the basis of the positional relationship between the two bright spot images and the alignment target. In the manual alignment, the main controller 211 displays the two bright spot images together with the observation image of the subject's eye E on the display 241, and the user operates the movement mechanism 150 using the operation device 242 while referring to the two bright spot images displayed.

The focus optical system 60 generates a split indicator used for the focus adjustment with respect to subject's eye E. In conjunction with the movement of the photography focusing lens 31 along the optical path of the photographing optical system 30 (referred to as the photographing optical path), the focus optical system 60 is moved along the optical path of the illumination optical system 10 (called the illumination optical path). The reflection rod 67 is inserted into and removed from the illumination optical path. Before performing focus adjustment, the reflective surface of the reflection rod 67 is arranged in the slanted state in the illumination optical path. The focus light output from the LED 61 passes through the relay lens 62, is split into two light beams by the split indicator plate 63, passes through the two-hole diaphragm 64. The focus light, then, is reflected by the mirror 65, is converged on the reflective surface of the reflection rod 67 by the condenser lens 66, and is reflected by the reflective surface. Further, the focus light travels through the relay lens 20, is reflected by the aperture mirror 21, and penetrates the dichroic mirror 46, thereby being projected onto the subject's eye E via the objective lens 22. The return light of the focus light from the subject's eye E (the fundus reflection light, etc.) passes through the same route as that of the return light of the alignment light and is guided to the image sensor 35. Based on the received image, manual focusing and/or automatic focusing can be performed. The received image is referred to as a split indicator image.

The diopter correction lenses 70 and 71 can be selectively inserted into the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for fundus photography and the optical path for OCT (measurement arm). The dichroic mirror 46 reflects the light of wavelength bands used for OCT and transmits the light for fundus photography. Listed from the OCT unit 100 side, the collimator lens unit 40, the retroreflector 41, the dispersion compensation member 42, the OCT focusing lens 43, the optical scanner 44, and the relay lens 45 are arranged in the measurement arm.

The retroreflector 41 is movable in the directions indicated by the arrow in FIG. 2, whereby the length of the measurement arm is changed. The change in the optical path length of the measurement arm may be utilized for correcting the optical path length according to the axial length, and for adjusting the interference condition, for example.

Together with the dispersion compensation member 113 (described later) arranged in the reference arm, the dispersion compensation member 42 acts to equalize the dispersion characteristics of the measurement light LS and the dispersion characteristics of the reference light LR with each other.

The OCT focusing lens 43 is moved along the measurement arm in order to perform the focus adjustment of the measurement arm. The movement of the photography focusing lens 31, the movement of the focus optical system 60, and the movement of the OCT focusing lens 43 may be controlled in an interlocking manner.

The optical scanner 44 is placed substantially at a position optically conjugate with the pupil of the subject's eye E. The optical scanner 44 deflects the measurement light LS guided through the measurement arm. The optical scanner 44 is, for example, a galvano scanner capable of two dimensional scanning. Typically, the optical scanner 44 includes an x-scanner (e.g., x-galvano mirror) that deflects the measurement light LS in the x direction and a y-scanner (e.g., y-galvano mirror) that deflects the measurement light LS in the y direction.

Figure 1B:
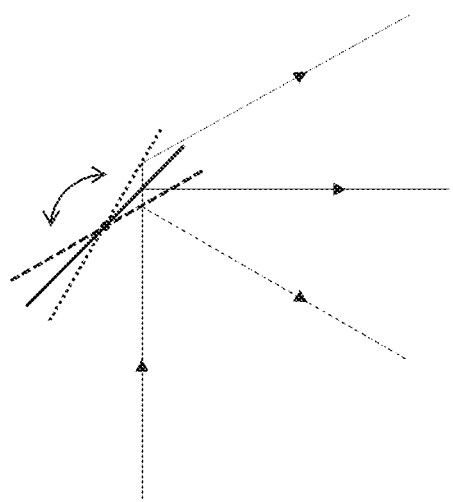
FIG. 1B is a schematic diagram for describing an error in phase information caused by an optical scanner for OCT scanning.

Note that the optical scanner 44 is not limited to a galvano scanner thus configured, and may include an optical deflector of another type. As described above, the optical scanner 44 includes a reflecting mirror configured to rotate about an axis. When the measurement light LS is reflected at a position off the rotation axis of the reflecting mirror (see FIG. 1B), the phase information changes, and the position of the reference point (zero point) of the blood flow velocity is shifted (deviated). This induces a measurement error.

Further, in the event that the optical scanner 44 in which two reflecting mirrors having different deflection directions are arranged in series (such as the optical scanner 44 provided with an x-scanner and a y-scanner) is employed, at least the reflecting mirror in the second place becomes a factor causing measurement errors. Although details will be described later, the present embodiment discloses a technique for eliminating (reducing) phase information error caused by the optical scanner 44 and eliminating (reducing) errors in hemodynamics measurements.

<OCT Unit 100>

Figure 3:
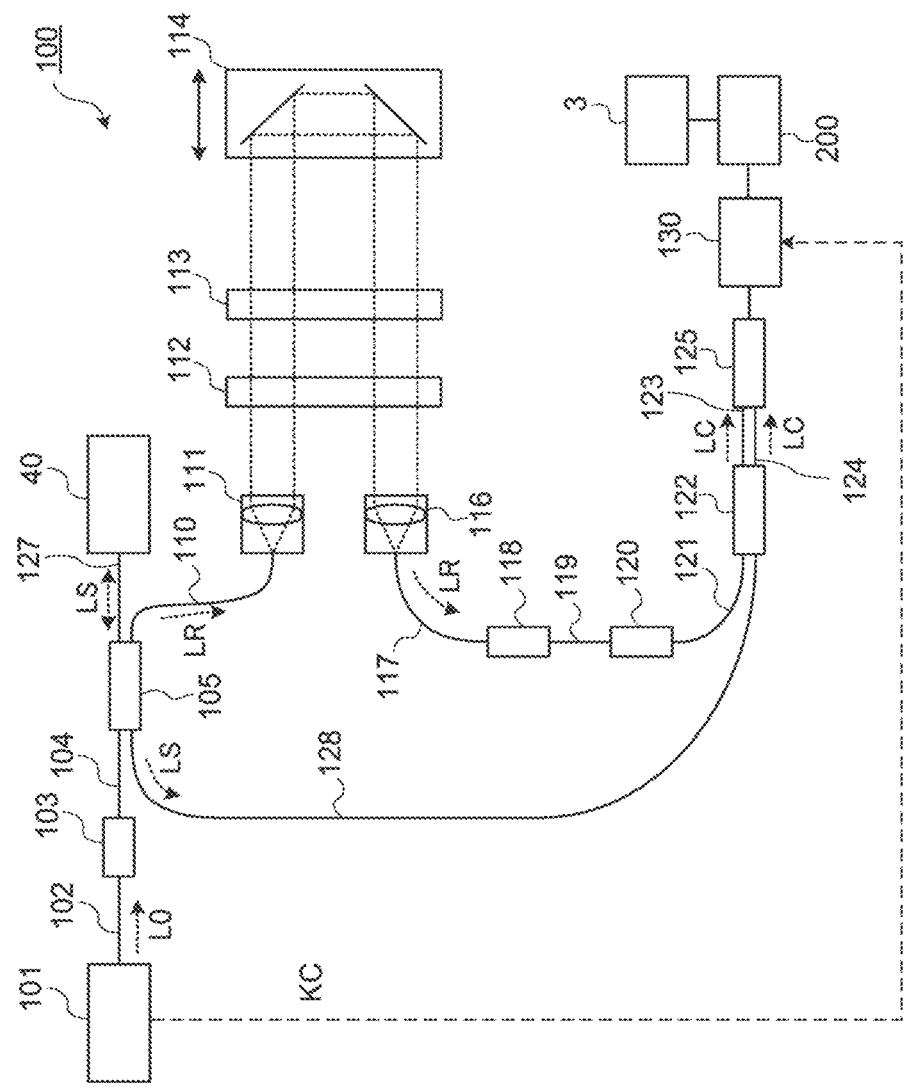
FIG. 3 is a schematic diagram showing an example of the configuration of the blood flow measurement apparatus (optical coherence tomography apparatus) of an exemplary aspect according to the embodiment.

As illustrated in FIG. 3, the OCT unit 100 is provided with the optical system for performing swept source OCT. The optical system includes an interference optical system. The interference optical system is configured to split the light emitted from the light source of wavelength tunable type (or wavelength sweeping type) into measurement light and reference light, superpose the return light of the measurement light from the subject's eye E and the reference light having traveled through the reference optical path to generate interference light, and detect the interference light. The detection result (i.e., detection signal) obtained by the interference optical system is a signal representing a spectrum of the interference light. The detection signal is sent to the arithmetic and control unit 200.

The light source unit 101 includes, for example, a near infrared tunable laser configured to change the wavelengths of emitted light at high speed. The light LO output from the light source unit 101 is guided to the polarization controller 103 through the optical fiber 102, and the polarization state of the light LO is regulated. Further, the light LO is guided to the fiber coupler 105 through the optical fiber 104 and is split into the measurement light LS and the reference light LR. The optical path of the measurement light LS is referred to as a measurement arm, a sample arm, or the like, and the optical path of the reference light LR is referred to as a reference arm or the like.

The reference light LR is guided through the optical fiber 110 to the collimator 111, is converted into a parallel light beam, travels through the optical path length correction member 112 and the dispersion compensation member 113, and is guided to the retroreflector 114. The optical path length correction member 112 acts to match the optical path length of the reference light LR and the optical path length of the measurement light LS with each other. The dispersion compensation member 113 acts to equalize the dispersion characteristics of the reference light LR and the dispersion characteristics of the measurement light LS with each other, together with the dispersion compensation member 42 arranged in the measurement arm. The retroreflector 114 is movable along the optical path of the reference light LR incident on the retroreflector 114. With this, the length of the reference arm is changed. The change in the optical path length of the reference arm can be utilized, for example, for the correction of the optical path length according to the axial length, and for the regulation of the interference condition.

The reference light LR that has passed through the retroreflector 114 travels through the dispersion compensation member 113 and the optical path length correction member 112, is converted from a parallel light beam to a convergent light beam by the collimator 116, and is incident on the optical fiber 117. The reference light LR incident on the optical fiber 117 is guided to the polarization controller 118, and the polarization state of the reference light LR is regulated. Then, the reference light LR is guided to the attenuator 120 through the optical fiber 119, and the light amount of the reference light LR is regulated. Subsequently, the reference light LR is guided to the fiber coupler 122 through the optical fiber 121.

Meanwhile, the measurement light LS generated by the fiber coupler 105 is guided through the optical fiber 127 and is converted to a parallel light beam by the collimator lens unit 40. Then, the measurement light LS passes through the retroreflector 41, the dispersion compensation member 42, the OCT focusing lens 43, the optical scanner 44, and the relay lens 45, and then reaches the dichroic mirror 46. The measurement light LS is reflected by the dichroic mirror 46, is refracted by the objective lens 22, and is projected onto the subject's eye E. The measurement light LS is reflected and scattered at various depth positions of the subject's eye E. The return light of the measurement light LS from the subject's eye E travels along the same route as the outward way in the opposite direction, is directed to the fiber coupler 105, and then reaches the fiber coupler 122 via the optical fiber 128.

The fiber coupler 122 superposes the measurement light LS incident through the optical fiber 128 and the reference light LR incident through the optical fiber 121 with each other, to generate interference light. The fiber coupler 122 splits the generated interference light at a predetermined splitting ratio (e.g., 1 to 1) to generate a pair of interference light LC. The pair of the interference light LC is guided to the detector 125 through the optical fibers 123 and 124, respectively.

The detector 125 includes, for example, a balanced photo diode. The balanced photodiode includes a pair of photodetectors for respectively detecting the pair of the interference light LC. The balanced photodiode outputs the difference between the pair of detection results obtained by the pair of photodetectors. The detector 125 sends the output (i.e., detection signal) to the data acquisition system (DAQ or DAS) 130.

The clock KC is supplied from the light source unit 101 to the data acquisition system 130. The clock KC is generated in the light source unit 101 in synchronization with the output timings of the respective wavelengths varied within a predetermined wavelength range by the wavelength tunable type light source. For example, the light source unit 101 splits the light LO of each output wavelength to generate two pieces of split light, optically delays one of the two pieces of split light, combines the two pieces of split light, detects the combined light obtained, and generates the clock KC based on the result of the detection of the combined light. The data acquisition system 130 performs the sampling of the detection signal input from the detector 125 based on the clock KC. The data acquisition system 130 sends the result of the sampling of the detection signal from the detector 125 to the arithmetic and control unit 200.

The present example is provided with both an element for changing the optical path length of the measurement arm (e.g., the retroreflector 41) and an element for changing the optical path length of the reference arm (e.g., the retroreflector 114 or a reference mirror). However, only one of these elements may be provided in other embodiments. Elements for changing the difference between the optical path length of the measurement arm and the optical path length of the reference arm (i.e., elements for changing the optical path length difference) are not limited to the aforesaid elements, and may be any type of element such as any type of optical members and any type of mechanisms.

<Processing System>

Figure 4:
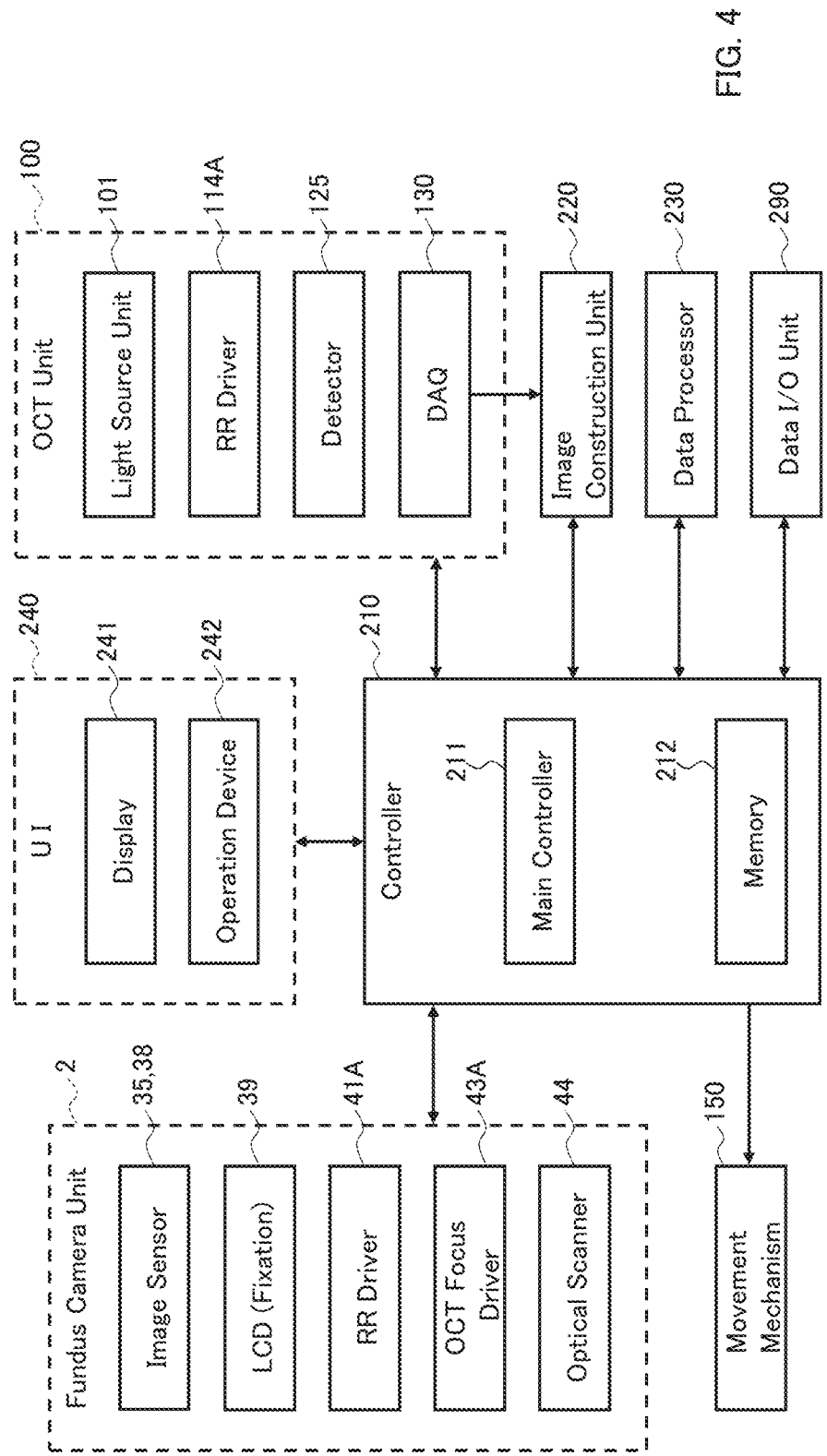
FIG. 4 is a schematic diagram showing an example of the configuration of the blood flow measurement apparatus (optical coherence tomography apparatus) of an exemplary aspect according to the embodiment.
Figure 5:
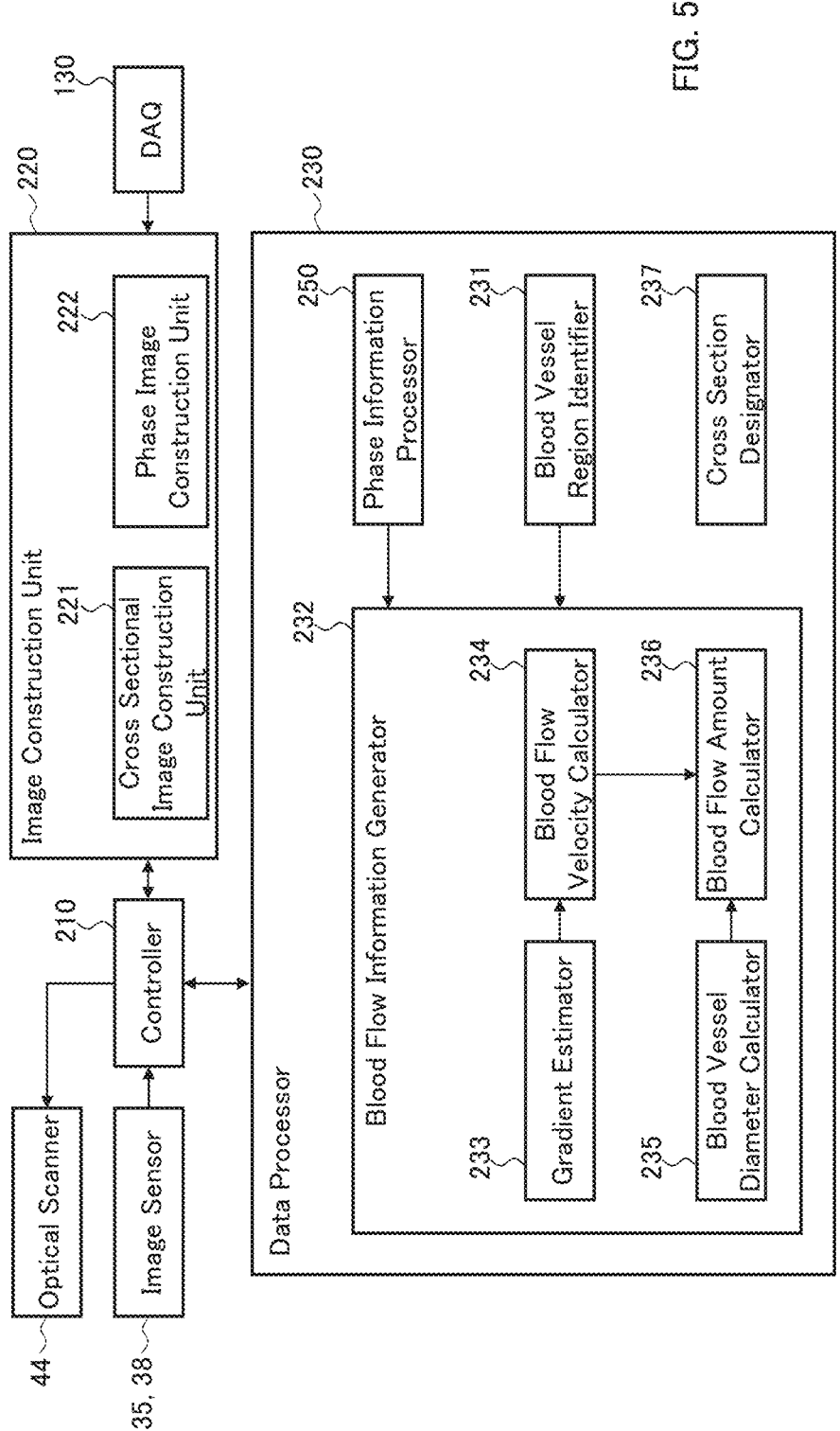
FIG. 5 is a schematic diagram showing an example of the configuration of the blood flow measurement apparatus (optical coherence tomography apparatus) of an exemplary aspect according to the embodiment.

FIG. 4 and FIG. 5 show an example of the configuration of the processing system (arithmetic and control system) of the blood flow measurement apparatus 1. The controller 210, the image construction unit 220 and the data processor 230 are provided in the arithmetic and control unit 200.

<Controller 210>

The controller 210 performs various kinds of controls. The controller 210 includes the main controller 211 and the memory 212.

<Main Controller 211>

The main controller 211 includes a processor operable according to a control program, and controls each unit and element of the blood flow measurement apparatus 1 (including the units and elements shown in FIG. 2 to FIG. 5).

The photography focusing lens 31 disposed in the photographing optical path and the focus optical system 60 disposed in the illumination optical path are moved in a synchronized manner by a photographing focus driver (not shown) under the control of the main controller 211. The retroreflector 41 disposed in the measurement arm is moved by the retroreflector driver (RR driver) 41A under the control of the main controller 211. The OCT focusing lens 43 disposed in the measurement arm is moved by the OCT focus driver 43A under the control of the main controller 211. The retroreflector 114 disposed in the reference arm is moved by the retroreflector driver (RR driver) 114A under the control of the main controller 211. Each of the aforesaid drivers includes an actuator such as a pulse motor which operates under the control of the main controller 211. The optical scanner 44 disposed in the measurement arm operates under the control of the main controller 211.

The movement mechanism 150 moves, for example, at least the fundus camera unit 2 in a three dimensional manner. In a typical example, the movement mechanism 150 includes the followings: an x stage movable in the ±x direction (i.e., left and right direction); an x movement mechanism that moves the x stage; a y stage movable in the ±y direction (i.e., up and down direction); a y movement mechanism that moves the y stage; a z stage movable in the ±z direction (i.e., depth direction); and a z movement mechanism that moves the z stage. Each of the aforesaid movement mechanisms includes an actuator such as a pulse motor which operates under the control of the main controller 211.

The main controller 211 controls the LCD 39. For example, the main controller 211 displays the fixation target at a preset position on the screen of the LCD 39. Further, the main controller 211 may change the display position of the fixation target displayed on the LCD 39. That is, the main controller 211 may change the fixation position. The fixation target movement may be performed in any manner such as continuous movement, intermittent movement, and discrete movement. Some exemplary manners of moving the fixation position in the present embodiment will be described later.

The fixation position is represented by the display position (the pixel coordinates) of the fixation target image on the LCD 39, for example. The pixel coordinates are defined, for example, by using coordinates represented by a two dimensional coordinate system predefined on the display screen of the LCD 39. If the aforementioned fixation matrix device is used, the fixation position is represented, for example, by the position (coordinates) of the light emitting part lit for fixation. The coordinates of that light emitting part are, for example, the coordinates represented by a two dimensional coordinate system defined in advance on the plane on which the plurality of light emitting parts are arranged.

<Memory 212>

The memory 212 stores various kinds of data. Examples of the data stored in the memory 212 include OCT images, fundus images, and subject's eye information. The subject's eye information includes subject information such as the patient ID and the patient's name, identification information for the left eye and the right eye, and electronic medical record information.

<Image Construction Unit 220>

The image construction unit 220 constructs OCT image data of the fundus Ef based on the signal (sampling data, or sampled data) input from the data acquisition system 130. The image construction unit 220 may construct B-scan image data (i.e., two dimensional cross sectional image data) and phase image data of the fundus Ef. These pieces of OCT image data will be described later. The image construction unit 220 includes, for example, a processor operable according to an image constructing program. In the present specification, "image data" and an "image" displayed or rendered based thereon may not be distinguished from one another unless otherwise mentioned.

The blood flow measurement of the present embodiment performs two types of scans on the fundus Ef. The two types of scans will be referred to as a main scan and a supplementary scan.

The main scan performs repetitive scanning (iterative scanning), with the measurement light LS, on a cross section of the fundus Ef that intersects a blood vessel of interest, to acquire intensity information (e.g., cross sectional image data) and phase information (e.g., phase image data). Such a cross section to which the main scan is applied is referred to as a cross section of interest. In some examples, the main scan performs a first scan and a second scan. The first scan is operated to scan the cross section of interest in a first scan direction. The second scan is operated to scan the cross section of interest in a second scan direction that is opposite to the first scan direction. Hereinafter, some examples will be described of aspects of the main scan that are applicable to the present embodiment. Two or more of these examples may be combined together. Exemplary main scans are performed under the control of the main controller 211.

Figure 6A:
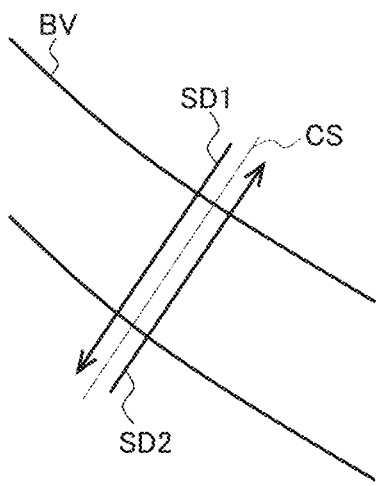
FIG. 6A is a schematic diagram for describing an example of the operation of the blood flow measurement apparatus (optical coherence tomography apparatus) of an exemplary aspect according to the embodiment.

FIG. 6A shows an example of the main scan. The main scan of the present example includes the first scan and the second scan as follows. The first scan is operated to scan the cross section of interest CS that intersects the blood vessel of interest BV in the first scan direction SD1. The second scan is operated to scan the cross section of interest CS in the second scan direction SD2 opposite to the first scan direction SD1. The first scan is performed once or more, and the second scan is also performed once or more.

In the main scan of the present example, the cross section to which the first scan is applied and the cross section to which the second scan is applied are the same. Note that the actual position for the scan to be applied may vary because of eye movements, body motions, or pulsations; however, optical system tracking or scan tracking may cancel, eliminate, or reduce the variation in the position for the scan to be applied.

Figure 6B:
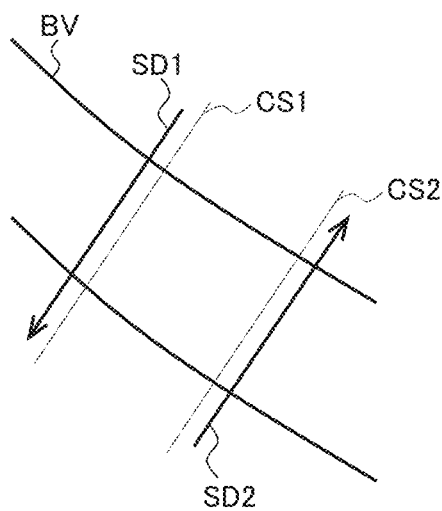
FIG. 6B is a schematic diagram for describing an example of the operation of the blood flow measurement apparatus (optical coherence tomography apparatus) of an exemplary aspect according to the embodiment.

FIG. 6B shows another example of the main scan. In the main scan of the present example, the cross section to which the first scan is applied and the cross section to which the second scan is applied are different from each other. The main scan of the present example includes the first scan and the second scan as follows. The first scan is operated to scan the first cross section of interest CS1 that intersects the blood vessel of interest BV in the first scan direction SD1. The second scan is operated to scan the second cross section of interest CS2 that is different from the first cross section of interest CS1 in the second scan direction SD2 opposite to the first scan direction SD1. The first scan is performed once or more, and the second scan is also performed once or more.

There may be two or more cross sections to which the first scan is applied, and two or more cross sections to which the second scan is applied. Further, at least one of one or more cross sections to which the first scan is applied and at least one of one or more cross sections to which the second scan is applied may be the same.

Figure 6C:
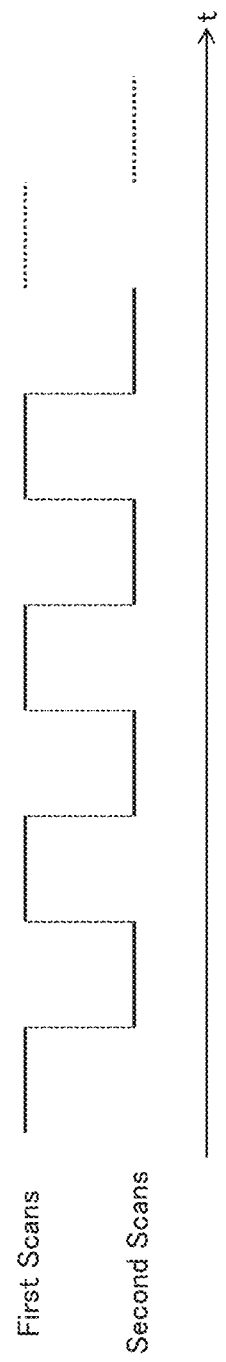
FIG. 6C is a schematic diagram for describing an example of the operation of the blood flow measurement apparatus (optical coherence tomography apparatus) of an exemplary aspect according to the embodiment.

FIG. 6C shows an example of the main scan. In the present example, a single first scan and a single second scan are performed in an alternate manner. Applying such alternating scans of the present example to a single cross section (e.g., the cross section of interest CS shown in FIG. 6A) corresponds to repeatedly scanning this cross section in a reciprocating manner.

The number of executions of the first scan and the number of executions of the second scan may be set in advance. Alternatively, the execution time length of the alternating scans may be set in advance. In some example, the alternating scans may be started in response to an instruction from the user, and/or the alternating scans may be finished in response to an instruction from the user. On the other hand, the alternating scan may be started and/or finished under automatic control. The automatic control may be realized by combining the blood flow measurement apparatus 1 with, for example, an electrocardiograph, live OCT (real-time OCT), or live blood flow measurement (real-time blood flow measurement).

As described above, the main scan illustrated in FIG. 6C performs one first scan and one second scan in an alternate manner. More generally, one or more first scans and one or more second scans may be performed in an alternate manner. For example, two consecutive first scans and two consecutive second scans may be alternately performed, or one first scan and two consecutive second scans may be alternately performed. Further, in such alternating scans, the number of consecutive first scans may or may not be constant, and/or the number of consecutive second scans may or may not be constant.

The aspects of the main scan that performs both a plurality of first scans and a plurality of second scans are not limited to alternating scans. For example, a plurality of second scans may be performed after a plurality of first scans has been performed. In general, the main scan that performs both a plurality of first scans and a plurality of second scans corresponds to repeatedly performing each of the first scan and the second scan, in other words, corresponds to a combination of the plurality of first scans and the plurality of second scans in an arbitrary order.

The supplementary scan performs a scan on a predetermined cross section with the measurement light LS in order to estimate the gradient (or, inclination, tilt, slope, slant, or the like) of the blood vessel of interest at the cross section of interest. The cross section to which the supplementary scan is applied is referred to as a supplementary cross section. In some examples, the supplementary cross section may be a cross section that intersects the blood vessel of interest and is located in the vicinity of the cross section of interest. Such a supplementary cross section is referred to as the first supplementary cross section. In some other examples, the supplementary cross section may be a cross section that intersects the cross section of interest and is oriented along the blood vessel of interest. Such a supplementary cross section is referred to as the second supplementary cross section.

Figure 7A:
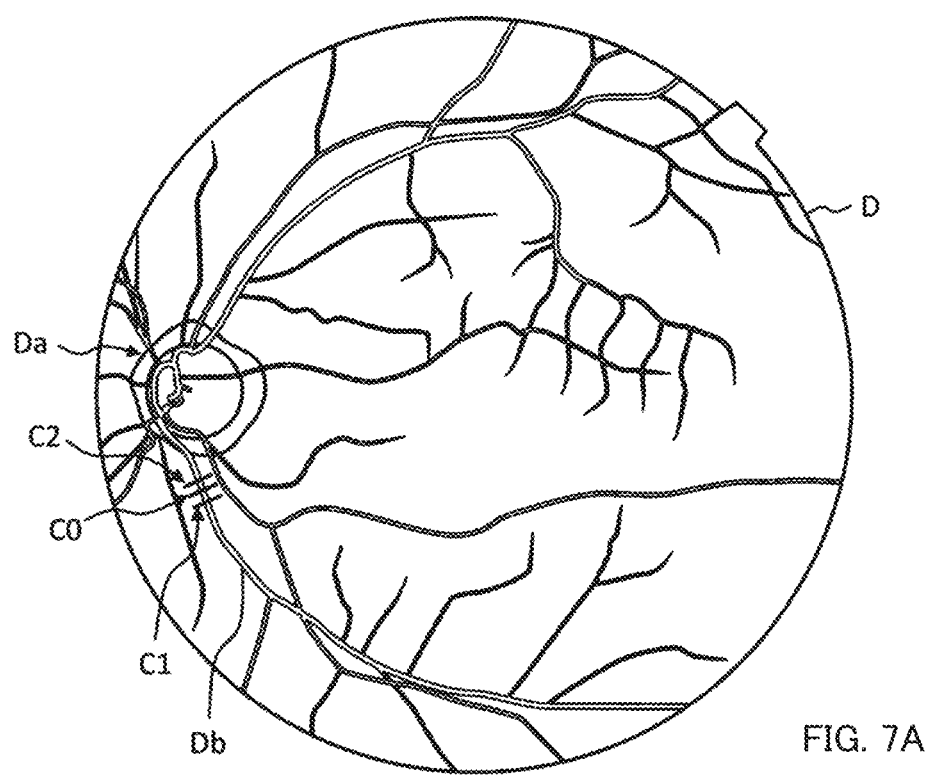
FIG. 7A is a schematic diagram for describing an example of the operation of the blood flow measurement apparatus (optical coherence tomography apparatus) of an exemplary aspect according to the embodiment.

FIG. 7A shows an example in which the first supplementary cross section is employed. In the present example, as shown on the fundus image D, one cross section of interest C0 and two supplementary cross sections C1 and C2 are set to intersect the blood vessel of interest Db. Here, the cross section of interest C0 is located near the optic nerve head Da of the fundus Ef, and the supplementary cross sections C1 and C2 are located near the cross section of interest C0. One of the two supplementary cross sections C1 and C2 is located on the upstream side of the blood vessel of interest Db with respect to the cross section of interest C0, and the other is located on the downstream side. The cross section of interest C0 and the supplementary cross sections C1 and C2 are each oriented to be substantially orthogonal to the running direction of the blood vessel of interest Db, for example.

Figure 7B:
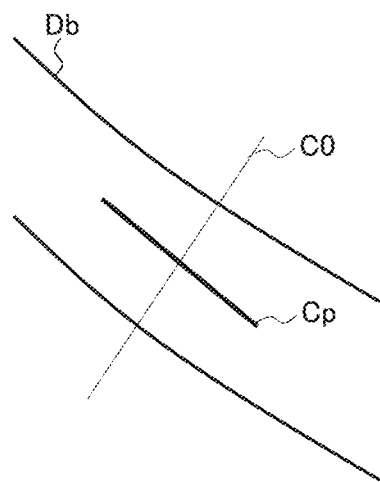
FIG. 7B is a schematic diagram for describing an example of the operation of the blood flow measurement apparatus (optical coherence tomography apparatus) of an exemplary aspect according to the embodiment.

FIG. 7B shows an example in which the second supplementary cross section is employed. Similar to the above example shown in FIG. 7A, the cross section of interest C0 is set to be substantially orthogonal to the blood vessel of interest Db in the present example. Further, in the present example, the supplementary cross section Cp is set to be substantially orthogonal to the cross section of interest C0. The supplementary cross section Cp is oriented along the blood vessel of interest Db. As an example, the supplementary cross section Cp may be set to pass through the intersection between the central line of the blood vessel of interest Db and the cross section of interest C0.

In the exemplary blood flow measurement, the main scan performs repetitive scanning over a period of time containing at least one cardiac cycle of the patient's heart. This makes it possible to obtain blood flow dynamics information for all cardiac phases. The period of time during which the main scan is performed may be a fixed length of time set in advance, or a length of time set for a target patient or an examination to be conducted. In the former case (fixed length of time), a period of time longer than the standard cardiac cycle is set (e.g., 2 seconds). In the latter case (non-fixed length of time), biometric data (medical parameters) such as the patient's electrocardiogram may be referred to. Here, any factor other than cardiac cycles may be considered. Examples of such factors include the length of time required for conduction of examination (e.g., burden on patients), the response time of the optical scanner 44 (e.g., scanning time interval), the response time of the detector 125 (e.g., scanning time interval), and the like.

The image construction unit 220 includes the cross sectional image construction unit 221 and the phase image construction unit 222.

<Cross Sectional Image Construction Unit 221>

The cross sectional image construction unit 221 constructs cross sectional images that represents a temporal change (or, temporal variation, chronological change, chronological variation, time course, or the like) in the morphology (or structure) of the cross section of interest, based on sampling data obtained by the data acquisition system 130 with the main scan. Such a cross sectional image is referred to as a main cross sectional image. This cross sectional image construction process will be described in more detail. As described above, the main scan performs repetitive scanning on the cross section of interest. Sampling data is sequentially input from the data acquisition system 130 to the cross sectional image construction unit 221 in response to the repetition of scans. The cross sectional image construction unit 221 constructs one main cross sectional image corresponding to the cross section of interest C0, based on the sampling data corresponding to one scan performed on the cross section of interest C0. The cross sectional image construction unit 221 repeats such processing as many times as the number of repetition of scans in the main scan, to construct a series of main cross sectional images in time series. Here, these main cross sectional images may be put into a plurality of groups, and then two or more main cross sectional images belonging to one group may be synthesized or composed to create an image having improved image quality. Such processes are referred to as image averaging.

Further, the cross sectional image construction unit 221 constructs a cross sectional image that represents the morphology (or structure) of the supplementary cross section, based on sampling data obtained by the data acquisition system 130 with the supplementary scan for the supplementary cross section(s). Such a cross sectional image is referred to as a supplementary cross sectional image. The supplementary cross sectional image constructing process may be executed in the same manner as the main cross sectional image constructing process described above. Here, the main cross sectional image is a series of cross sectional images in time series, but the supplementary cross sectional image may be one cross sectional image. Further, the supplementary cross sectional image may be an image having improved image quality created by synthesizing or composing a plurality of cross sectional images acquired by a plurality of scans on the supplementary cross section (image averaging).

When the supplementary cross sections C1 and C2 illustrated in FIG. 7A are employed, the cross sectional image construction unit 221 constructs a supplementary cross sectional image corresponding to the supplementary cross section C1 and a supplementary cross sectional image corresponding to the supplementary cross section C2. On the other hand, when the supplementary cross section Cp illustrated in FIG. 7B is employed, the cross sectional image construction unit 221 constructs a supplementary cross sectional image corresponding to the supplementary cross section Cp.

The process of constructing a cross sectional image as described thus far includes noise elimination (noise reduction), filtering, and fast Fourier transform (FFT) similarly to the generation of intensity information (amplitude information) in conventional Fourier domain OCT techniques. By applying fast Fourier transform, sampling data obtained by the data acquisition system 130 (i.e., interference signal, interferogram) is converted into an A-line profile. Such an A-line profile is a reflection intensity profile along the z direction. By performing imaging process on the A-line profile, that is, by assigning pixel values to the reflection intensity values in the A-line profile, an A-scan image is generated. Further, a two dimensional cross sectional image such as a B-scan image or a circle scan image is constructed by arranging a plurality of the A-scan images thus generated according to the scan pattern. In the case where an OCT apparatus of another type is employed, the cross sectional image construction unit 221 executes a known process according to the OCT type employed.

<Phase Image Construction Unit 222>

The phase image construction unit 222 constructs a phase image that represents a temporal change (or, temporal variation, chronological change, chronological variation, time course, or the like) in the phase differences in the cross section of interest, based on sampling data obtained by the data acquisition system 130 with the main scan. The phase image is an example of phase information. The sampling data used for constructing the phase image may be the same as the sampling data used for constructing the main cross sectional image by the cross sectional image construction unit 221. Doing so makes it possible to perform registration between the main cross sectional image and the phase image. In other words, a natural correspondence may be defined between the pixels of the main cross sectional image and the pixels of the phase image.

An example will be described of a method of constructing such phase images. A phase image in the present example is obtained by calculating the phase difference between adjacent A-line complex signals (that is, signals corresponding to mutually adjacent scan points). In other words, the phase image in the present example is constructed based on the temporal change in the pixel values (brightness values) of the main cross sectional image. For an arbitrary pixel of the main cross sectional image, the phase image construction unit 222 creates a graph of the temporal change in the brightness value of that pixel. The phase image construction unit 222 determines the phase difference $\Delta\varphi$ between two time points t1 and t2 separated by a predetermined time interval $\Delta t$ in the graph created (t2=t1+$\Delta t$). Then, the phase difference $\Delta\varphi$ is defined as the phase difference $\Delta\varphi$(t1) at the time point t1. More generally, the phase difference $\Delta\varphi$ may be defined as the phase difference at an arbitrary time point between the time points t1 and t2. By performing this process for each of a large number of time points set in advance, a temporal change in the phase difference for that pixel is obtained.

A phase image is an image representation of phase difference values of each pixel at each time point. This imaging process may be realized, for example, by representing the values of the phase difference with display colors or brightness. When applying such image representation, a display color indicating that a phase has increased in time series may be different from a display color indicating that a phase has decreased in time series. For example, red is assigned to phase increase, and blue is assigned to phase decrease. Further, the magnitude of the amount of change in a phase may be represented by the density of display colors. By adopting representation methods as described above, the direction and quantity of blood flow may be clearly indicated using display colors. A phase image is constructed by executing the above processing for each pixel.

Note that the temporal change in phase difference may be obtained by sufficiently reducing the time interval $\Delta t$ described above to secure the correlation in phases. Here, oversampling may be performed in which the time interval $\Delta t$ is set to a value less than the time period corresponding to the resolution of a cross sectional image in the scanning of the measurement light LS.

In the event that the main scan including a plurality of first scans and a plurality of second scans is performed as described above with reference to FIG. 6C, the phase image construction unit 222 generates a plurality of pieces of first phase information and a plurality of pieces of second phase information. The plurality of pieces of first phase information is generated from a plurality of pieces of first acquisition data acquired by the plurality of first scans. Also, the plurality of pieces of second phase information is generated from a plurality of pieces of second acquisition data acquired by the plurality of second scans.

Typically, the phase image construction unit 222 generates a plurality of pieces of first phase information respectively from a plurality of pieces of first acquisition data respectively acquired by a plurality of first scans. Also, the phase image construction unit 222 generates a plurality of pieces of second phase information respectively from a plurality of pieces of second acquisition data respectively acquired by a plurality of second scans. In other words, the phase image construction unit 222 generates the same number of pieces of first phase information from the same number of pieces of first acquisition data as the number of executions of first scan. Also, the phase image construction unit 222 generates the same number of pieces of second phase information from the same number of pieces of second acquisition data as the number of executions of second scan. More generally, the phase image construction unit 222 may be configured to generate the number of pieces of first phase information less than or equal to the number of executions of the first scan, and generate the number of pieces of second phase information less than or equal to the number of executions of the second scan.

<Data Processor 230>

The data processor 230 performs various kinds of data processing. For example, the data processor 230 applies various kinds of image processing and/or various kinds of image analysis, to an image constructed by the image construction unit 220. Further, the data processor 230 may perform various kinds of image processing and/or various kinds of image analysis, on an image obtained by the fundus camera unit 2 (e.g., a fundus image, an anterior eye segment image), an image input from the outside, or other images.

The data processor 230 may construct three dimensional image data of the fundus Ef. Three dimensional image data means image data in which the positions of pixels are defined using a three dimensional coordinate system. Stack data and volume data are examples of such three dimensional image data. Stack data is image data constructed by arranging a plurality of cross sectional images respectively obtained for a plurality of scan lines in an three dimensional fashion, based on the positional relationship of the scan lines. In other words, stack data is image data constructed by representing a plurality of cross sectional images, which are originally defined using mutually different two dimensional coordinate systems, using a common three dimensional coordinate system. In further other words, stack data is image data constructed by embedding such a plurality of cross sectional images in a common three dimensional space. Volume data is image data whose picture elements are voxels that are arranged in a three dimensional manner. Volume data is also referred to as voxel data. Volume data is constructed by applying known interpolation, voxelization, or the like, to stack data.

The data processor 230 may construct an image to be displayed, by applying rendering to three dimensional image data. Examples of applicable rendering methods and techniques include volume rendering, surface rendering, maximum intensity projection (MIP), minimum intensity projection (MinIP), and multi planar reconstruction (MPR).

The data processor 230 includes the following exemplary elements for obtaining blood flow information: the blood vessel region identifier 231, the blood flow information generator 232, and the cross section designator 237. The blood flow information generator 232 includes the gradient estimator 233, the blood flow velocity calculator 234, the blood vessel diameter calculator 235, and the blood flow amount calculator 236. In addition, the data processor 230 includes the phase information processor 250 that processes a phase image constructed by the phase image construction unit 222.

<Phase Information Processor 250>

The phase information processor 250 generates one phase image based on two or more phase images constructed by the phase image construction unit 222. In other words, the phase information processor 250 composes two or more phase images. The phase image generated by the phase information processor 250 is referred to as a composite phase image. The composite phase image is an example of composite phase information based on two or more pieces of phase information.

Description will be provided in more detail. As described above, the main scan of the present embodiment performs the first scan at least once and the second scan at least once. Here, the first scan is operated to scan the cross section of interest of the fundus Ef in the first scan direction, and the second scan is operated to scan the cross section of interest in the second scan direction. The second scan direction is opposite to the first scan direction. The phase image construction unit 222 constructs at least one first phase image and at least one second phase image. The at least one first phase image is constructed based on at least one piece of first acquisition data acquired by at least one first scan. The at least one second phase image is constructed based on at least one piece of second acquisition data acquired by at least one second scan. The phase information processor 250 generates a composite phase image, based on any one or more of the at least one first phase image and any one or more of the at least one second phase image.

The phase information processor 250 generates a composite phase image, for example, by averaging a first phase image and a second phase image. The averaging operation here may be typically an arithmetic mean (averaging). Also, the averaging operation may be either a simple mean or a weighted mean.

The phase information processor 250 may be configured to perform the averaging operation after preprocessing. The preprocessing here includes, for example, registration between a first phase image and a second phase image. The registration is performed on a pixel-by-pixel basis. More specifically, the registration is a process of determining the correspondence between the pixels of a first phase image and the pixels of a second phase image. The averaging operation (more generally, image composition) is performed on pixels associated with each other by the registration.

The first scan and the second scan correspond to opposite scan directions to each other. For example, when applying the first scan and the second scan to the same cross section, the order of the arrangement of a plurality of pieces of A-scan image data generated from the first scan and the order of the arrangement of a plurality of pieces of A-scan image data generated from the second scan become opposite to each other. Rearrangement of such A-scan image data group is executed by, for example, the phase image construction unit 222 or the phase information processor 250.

When the above-described alternating scan (or reciprocating scan that is an exemplary aspect thereof) is applied, composite phase information may be generated based on the first phase information and the second phase information respectively corresponding to the first scan and the second scan performed consecutively. For example, the phase information processor 250 may generate a composite phase image based on the followings: the first phase image corresponding to one first scan of a plurality of first scans (i.e., the first phase information generated based on acquisition data obtained by the first scan); and the second phase image corresponding to the second scan performed immediately before or immediately after the first scan.

More generally, in the event that the main scan including a plurality of the first scans and a plurality of the second scans is performed, the phase information processor 250 may generate a composite phase image based on the first phase image and the second phase information. Here, the first phase image corresponds to one first scan of the plurality of first scans, and the second phase information corresponds to the second scan in which the difference in execution timing (or, time difference, time lag, or the like) with respect to the first scan is less than or equal to a preset threshold value. For example, the execution timing of a scan may be defined by a scale (dimension) of either time or scan order. The threshold for determining the difference between the execution timing of the first scan and the execution timing of the second scan may also be set using the same scale in advance.

In some examples, a first scan and a second scan are associated with each other in such a manner that the time difference between the execution time of the first scan and the execution time of the second scan is equal to or less than a predetermined length of time. Then, a first phase image and a second phase image respectively constructed from the first scan and the second scan associated with each other are composed. In some alternative examples, a first scan and a second scan are associated with each other in such a manner that the difference between the ordinal number of the first scan and the ordinal number of the second scan is equal to or less than a predetermined number. Here, the ordinal numbers are defined by a scan sequence as shown in FIG. 6C. Then, a first phase image and a second phase image respectively constructed from the first scan and the second scan associated with each other are composed.

When measuring an object that exhibits a substantially periodic change, the phase information processor 250 may combine the first phase information and the second phase information corresponding to mutually substantially the same time phase in the substantially periodic change.

For example, the present embodiment measures blood flow exhibiting a substantially periodic change, and the phase information processor 250 may generate a composite phase image on the basis of a first phase image and a second phase image as follows: the first phase image corresponds to a first scan performed at a time phase in the periodic change in hemodynamics, for example, at the time phase corresponding to the R wave in an electrocardiogram; and the second phase image corresponds to a second scan performed at a time phase substantially the same as the above time phase for the first scan, for example, at the time phase corresponding to the R wave.

The modes or aspects of processing executed by the phase information processor 250 are not limited to the examples described thus far. The modes or aspects of processing executed by the phase information processor 250 may be determined, selected, modified, or changed according to any of the followings: the type or kind of an object to which OCT scanning is applied; the type of OCT techniques; the mode or aspect of OCT scanning; the mode or aspect of phase information generation; and/or other factors.

Any of the processes described below, particularly any of the processes executed by the blood flow information generator 232, is applied to phase information (e.g., composite phase image) generated by the phase information processor 250. Note that at least part of the processing described below may be applied to phase information that has not been processed by the phase information processor 250. In other words, at least part of the processing described below may be applied to a phase image constructed by the phase image construction unit 222.

<Blood Vessel Region Identifier 231>

For each of the main cross sectional image, the supplementary cross sectional image, and the phase image (the composite phase image), the blood vessel region identifier 231 identifies a blood vessel region in that image corresponding to the blood vessel of interest Db. Such segmentation may be performed by analyzing the pixel values of at image (e.g., thresholding).

Note that although the main cross sectional image and the supplementary cross sectional image have sufficient resolution to be subjected to analysis processing, the phase image (the composite phase image) may not have the resolution enough to identify the boundary of a blood vessel region in some cases. However, since blood flow information is generated based on the phase image (the composite phase image), it is necessary to identify a blood vessel region included therein with high precision and high accuracy. To do so, for example, the following processes may be employed to more accurately identify a blood vessel region in the phase image (the composite phase image).

As described above, the main cross sectional image and the phase image (the composite phase image) are constructed from the same sampling data. Therefore, a natural correspondence between the pixels of the main cross sectional image and the pixels of the phase image (the composite phase image) may be defined. For example, the blood vessel region identifier 231 may be configured to perform the following processes to identify a blood vessel region in the phase image (the composite phase image): analyzing the main cross sectional image to identify a blood vessel region therein; identifying an image region in the phase image (the composite phase image) corresponding to the blood vessel region identified in the main cross sectional image based on the pixel correspondence described above; and adopting the image region identified in the phase image (the composite phase image) as a blood vessel region therein. Such processed make it possible to identify a blood vessel region in the phase image (the composite phase image) with high precision and high accuracy.

<Blood Flow Information Generator 232>

The blood flow information generator 232 generates blood flow information on the blood vessel of interest Db. As described above, the blood flow information generator 232 includes the gradient estimator 233, the blood flow velocity calculator 234, the blood vessel diameter calculator 235, and the blood flow amount calculator 236.

<Gradient Estimator 233>

The gradient estimator 233 derives an estimated value of the gradient of the blood vessel of interest Db based on data of the supplementary cross section (e.g., cross sectional data, supplementary cross sectional image) acquired by the supplementary scan described above. The estimated gradient value may be, for example, a measured value of the gradient of the blood vessel of interest Db at the cross section of interest, or an approximate value thereof.

An example is described of the case in which the gradient value of the blood vessel of interest Db is actually measured (the first example of gradient estimation). In the case where the supplementary cross sections C1 and C2 shown in FIG. 7A are applied, the gradient estimator 233 may calculate the gradient value of the blood vessel of interest Db at the cross section of interest C0, based on the positional relationship between the cross section of interest C0, the supplementary cross section C1, and the supplementary cross section C2, and further based on the result of identification of the blood vessel regions obtained by the blood vessel region identifier 231.

A method of calculating the gradient of the blood vessel of interest Db will be described with reference to FIG. 8A. The reference characters G0, G1 and G2 indicate the main cross sectional image at the cross section of interest C0, the supplementary cross sectional image at the supplementary cross section C1, and the supplementary cross sectional image at the supplementary cross section C2, respectively. The reference characters V0, V1 and V2 indicate a blood vessel region in the main cross sectional image G0, a blood vessel region in the supplementary cross sectional image G1, and a blood vessel region in the supplementary cross sectional image G2, respectively. The z coordinate axis shown in FIG. 8A substantially coincides with the incident direction of the measurement light LS. Further, the distance between the main cross sectional image G0 (the cross section of interest C0) and the supplementary cross sectional image G1 (the supplementary cross section C1) is denoted by d, and the distance between the main cross sectional image G0 (the cross section of interest C0) and the supplementary cross sectional image G2 (the supplementary cross section C2) is also denoted by d. The interval between adjacent cross sectional images, that is, the interval between adjacent cross sections is referred to as a distance between cross sections.

The gradient estimator 233 may calculate the gradient A of the blood vessel of interest Db at the cross section of interest C0 based on the positional relationship between the three blood vessel regions V0, V1 and V2. This positional relationship is determined, for example, by connecting the three blood vessel regions V0, V1 and V2. As a specific example, the gradient estimator 233 may identify feature positions respectively of the three blood vessel regions V0, V1 and V2, and connect the feature positions. Examples of such a feature position include a center position, a center of gravity position, an uppermost location (i.e., the position having the smallest z coordinate value), a lowermost location (i.e., the position having the largest z coordinate value), and the like. Among these examples of feature positions, the identification of the uppermost location is considered to be the simplest processing. In addition, examples of methods of connecting the feature positions include a method of connecting with a line segment, a method of connecting with an approximate curve (e.g., spline curve, Bezier curve), and the like.

Further, the gradient estimator 233 calculates the gradient A based on the lines connecting the feature positions identified from the three blood vessel regions V0, V1 and V2. When connecting with line segments, for example, the gradient A may be calculated based on the gradient of the first line segment and the gradient of the second line segment. Here, the first line segment connects the feature position of the cross section of interest C0 and the feature position of the supplementary cross section C1, and the second line segment connects the feature position of the cross section of interest C0 and the feature position of the supplementary cross section C2. An example of this calculation processing may be operated to calculate the average value of the gradients of the two line segments. On the other hand, an example of connecting with an approximate curve may be operated to calculate the gradient of the approximate curve at the position where the approximate curve intersects the cross section of interest C0. Note that the distance between cross sections d may be used, for example, when the cross sectional images G0 to G2 are embedded in the xyz coordinate system in the process of determining a line segment or an approximate curve.

In the above examples, the blood vessel regions in three cross sections are taken into consideration; however, other examples may take two cross sections into consideration to calculate the gradient. As a specific example thereof, one of the gradient of the first line segment and the gradient of the second line segment mentioned above may be selected as a targeted gradient. Furthermore, the gradient A of the blood vessel of interest Db at the cross section of interest C0 may be calculated based on the two supplementary cross sectional images G1 and
G2.

In the above examples, a single value of the gradient is obtained, but two or more values of the gradient may be obtained respectively for two or more positions (or regions) in the blood vessel region V0. If this is the case, the two or more gradient values obtained may be used separately. Alternatively, the two or more gradient values obtained may be subjected to statistical processing to derive a statistic (e.g., the mean value, the maximum value, the minimum value, the median, the mode), and the statistic may be used as the gradient A.

An example is described of the case in which an approximate value of the gradient of the blood vessel of interest is calculated (the second example of gradient estimation). In the event that the supplementary cross section Cp shown in FIG. 7B is applied, the gradient estimator 233 may analyze the supplementary cross sectional image corresponding to the supplementary cross section Cp to calculate an approximate value of the gradient of the blood vessel of interest Db at the cross section of interest C0.

A method of approximating the gradient of the blood vessel of interest Db will be described with reference to FIG. 8B. The reference character Gp indicates a supplementary cross sectional image of the supplementary cross section Cp. The reference character A indicates the gradient of the blood vessel of interest Db at the cross section of interest C0, as in the example shown in FIG. 8A.

In the present example, the gradient estimator 233 may identify an image region corresponding to a predetermined tissue of the fundus Ef by analyzing the supplementary cross sectional image Gp. For example, the gradient estimator 233 may identify an image region M corresponding to the inner limiting membrane (ILM) that is a surface tissue of the retina. The image region M is referred to as an inner limiting membrane region. For example, any known segmentation processing may be used to the image region identification.

It is known that the internal limiting membrane and fundus blood vessels are substantially parallel to each other. The gradient estimator 233 calculates the gradient $A_{app}$ of the inner limiting membrane region M at the cross section of interest C0. The gradient $A_{app}$ of the inner limiting membrane region M at the cross section of interest C0 may be used as an approximate value of the gradient A of the blood vessel of interest Db at the cross section of interest C0.

Figure 8B:
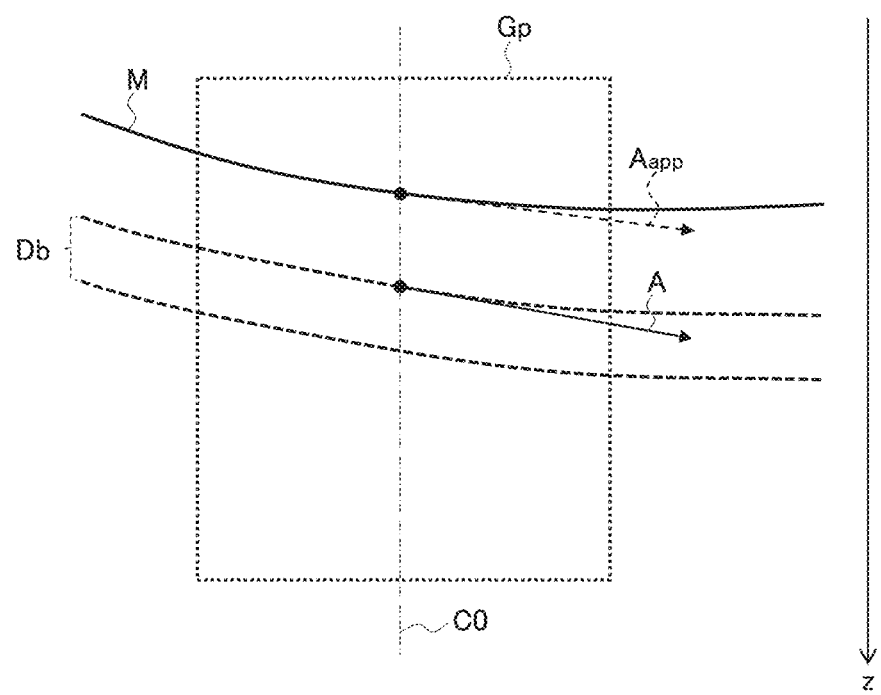
FIG. 8B is a schematic diagram for describing an example of the operation of the blood flow measurement apparatus (optical coherence tomography apparatus) of an exemplary aspect according to the embodiment.

Note that the gradient A shown in FIG. 8A and the gradient A shown in FIG. 8B are vectors representing the directions of the blood vessel of interest Db, and the definition of such vector values may be arbitrary. As an example, a value of the gradient A may be defined to be the angle formed by the gradient (vector) A and the z axis. Similarly, the gradient $A_{app}$ shown in FIG. 8B is a vector representing the orientation of the inner limiting membrane region M, and the definition of the value of the vector may be arbitrary. For example, the value of the gradient $A_{app}$ may be defined to be the angle formed by the gradient (vector) $A_{app}$ and the z axis. Note that the direction of the z axis is substantially the same as the incident direction of the measurement light LS.

In the third example of the gradient estimation of the blood vessel of interest, the gradient estimator 233 may analyze the supplementary cross sectional image Gp shown in FIG. 8B to identify an image region corresponding to the blood vessel of interest Db, and then calculate the gradient of the identified image region at the position corresponding to the cross section of interest C0. In such processing, the gradient estimator 233 may, for example, apply curve fitting to the boundary or the central axis of the image region corresponding to the blood vessel of interest Db, and then determine the gradient of the approximate curve, obtained by the curve fitting, at the position corresponding to the cross section of interest C0. A similar curve fitting technique may be applied to the image region corresponding to the predetermined tissue of the fundus Ef described above (e.g., the inner limiting membrane region M).

The processing executed by the gradient estimator 233 is not limited to the above processing examples, and may be any processing capable of deriving an estimated value of the gradient of the blood vessel of interest Db (e.g., a gradient value of the blood vessel of interest Db itself, a value approximating the gradient of the blood vessel of interest Db) based on cross sectional data acquired by applying OCT scanning to a cross section of the fundus Ef.

<Blood Flow Velocity Calculator 234>

Based on the temporal change in phase difference obtained as a phase image (a composite phase image), the blood flow velocity calculator 234 calculates the blood flow velocity (or blood flow rate) at the cross section of interest C0 for blood flowing in the blood vessel of interest Db. A parameter obtained by this calculation may be blood flow velocity at a certain time point, or may be a temporal change in blood flow velocity. The temporal change in blood flow velocity is referred to as blood flow velocity variation information. When blood flow velocity at a certain time point is to be determined, the blood flow velocity at a predetermined time phase in an electrocardiogram (e.g., a time phase corresponding to the R wave) may be selectively acquired, for example. When blood flow velocity variation information is to be determined, a time period during which blood flow velocity is measured is the whole or an arbitrary part of the time period taken for OCT scanning of the cross section of interest C0.

When the blood flow velocity variation information is acquired, the blood flow velocity calculator 234 may further calculate a statistic of the blood flow velocity in the measurement period. Examples of the statistic include the mean value, the standard deviation, the variance, the median, the mode, the global maximum, the global minimum, the local maximum, and the local minimum. The blood flow velocity calculator 234 may create a histogram on the blood flow velocity values.

The blood flow velocity calculator 234 calculates the blood flow velocity using Doppler OCT technique. In the blood flow velocity calculation, the gradient A (or its approximate value $A_{app}$) of the blood vessel of interest Db at the cross section of interest C0 calculated by the gradient estimator 233 is taken into account. More specifically, the blood flow velocity calculator 234 may be configured to use the following relationship.

$$\Delta f = \frac{2nv\cos\theta}{\lambda}$$

Here: Δf indicates the Doppler shift given to scattered light of the measurement light LS; n indicates the refractive index of medium; v indicates the flow velocity of the medium (blood flow velocity); θ indicates the angle between projection direction of the measurement light LS and the flow vector of the medium; and λ indicates the center wavelength of the measurement light LS.

In the present embodiment, n and λ are known, Δf is derived from the temporal change of the phase difference, and θ is derived from the gradient A (or, from the approximate gradient value $A_{app}$). Typically, θ is equal to the gradient A (or, to the approximate gradient value $A_{app}$). Substituting these values into the above equation yields the blood flow velocity v.

<Blood Vessel Diameter Calculator 235>

The blood vessel diameter calculator 235 calculates the diameter of the blood vessel of interest Db at the cross section of interest C0. Examples of the blood vessel diameter calculation include the first calculation method on the basis of a fundus image (a front image of an eye fundus) and the second calculation method on the basis of a cross sectional image.

When applying the first calculation method, an area of the fundus Ef including the location of the cross section of interest C0 is photographed in advance. A fundus image thus obtained may be an observation image (e.g., a frame(s) thereof), or may be a photographed image. When the photographed image is a color image, any image obtained from the color image (e.g., a red-free image) may be used. The photographed image may be a fluorescence image obtained by fundus fluorescence angiography (e.g., fluorescein angiography), or may be a blood vessel emphasized image obtained by OCT angiography. An image created using OCT angiography is also referred to as an angiogram or a motion contrast image.

The blood vessel diameter calculator 235 sets a scale for fundus images based on various kinds of factors used to determine the relationship between the scale for images and the scale in the real space. Examples of such factors include the photographing angle of view (photographing magnification), the working distance, information on an ocular optical system. The scale for fundus images may represents a length in the real space. As a specific example, the scale for fundus images may be configured to associate interval between adjacent pixels with a scale (distance) in the real space (e.g., pixel interval=10 μm). Note that it is possible to determine, in advance, the relationship between various values of the above factors and scales (values) in the real space, and then store a table or a graph that represents the relationship determined. In this case, the blood vessel diameter calculator 235 may select, from the table or the graph, a scale corresponding to the above factors and uses the scale selected.

Based on the scale and the pixels included in the blood vessel region V0, the blood vessel diameter calculator 235 calculates the diameter of the blood vessel of interest Db at the cross section of interest C0, that is, the diameter of the blood vessel region V0. As a specific example, the blood vessel diameter calculator 235 may calculate the maximum or the mean value of a plurality of diameters of the blood vessel region V0 corresponding to different directions. In some other examples, the blood vessel diameter calculator 235 may determine an approximate circle or an approximate ellipse of the contour of the blood vessel region V0, and then calculate the diameter of the approximate circle or the approximate ellipse. Note that once the blood vessel diameter of the blood vessel region V0 is determined, the area of the blood vessel region V0 can (substantially) be calculated. That is, it is possible to substantially associate blood vessel diameters with blood vessel areas in one-to-one fashion. Therefore, an area of a blood vessel may be calculated in place of a diameter of the blood vessel.

The second calculation method will be described. In the second calculation method, typically, a cross sectional image at the cross section of interest C0 is used. The cross sectional image may be a main cross sectional image or any other image.

The scale of the cross sectional image is determined based on OCT measurement conditions. In the present embodiment, the cross section of interest C0 is scanned as shown in FIG. 7A or FIG. 7B. The length of the cross section of interest C0 is determined based on various kinds of factors that define the relationship between the scale of an image and the scale in the real space such as the working distance and information about ocular optical system. The blood vessel diameter calculator 235, for example, determines the interval between adjacent pixels based on the length of the cross section of interest C0, and calculates the diameter of the blood vessel of interest Db at the cross section of interest C0 in the same manner as in the first calculation method.

<Blood Flow Amount Calculator 236>

Based on the calculation result of the blood flow velocity and the calculation result of the blood vessel diameter, the blood flow amount calculator 236 calculates a flow amount (or, flow volume) of blood that flows in the blood vessel of interest Db. An example of the blood flow amount calculation will be described below.

It is assumed that the blood flow in a blood vessel is the Hagen-Poiseuille flow. The blood vessel diameter is denoted by w, and the maximum blood flow velocity is denoted by Vm. Then, the blood flow amount Q is expressed as in the following equation.

$$Q = \frac{\pi w^2}{8} Vm$$

The blood flow amount calculator 236 substitutes the blood vessel diameter w calculated by the blood vessel diameter calculator 235 and the maximum blood flow velocity Vm based on the blood flow velocity calculated by the blood flow velocity calculator 234 into the above equation, thereby determining the targeted blood flow amount Q.

<Cross Section Designator 237>

The main controller 211 displays a front image of the fundus Ef on the display 241. The front image may be any type of image, and may be any of an observation image, a photographed image, a fluorescence image, an OCT angiography image, an OCT projection image, and an OCT shadowgram.

The user operates the operation device 242 to designate one or more cross sections of interest in the displayed front image of the fundus Ef. Each cross section of interest is designated to intersect a blood vessel of interest. Based on the designated one or more cross sections of interest and the front image of the fundus Ef, the cross section designator 237 may set one or more supplementary cross sections for each of the one or more cross sections of interest. Note that a supplementary cross section may be set manually.

In another example, the cross section designator 237 may be configured to analyze a front image of the fundus Ef to identify one or more blood vessels of interest. The identification of the blood vessels of interest is performed based on, for example, the thickness of a blood vessel, the positional relationship between a blood vessel and a predetermined site of a fundus (e.g., the optic nerve head, the macula), the type of a blood vessel (e.g., artery or vein), or the like. In addition, the cross section designator 237 may set one or more cross sections of interest and one or more supplementary cross sections, for each of the one or more blood vessels of interest identified.

In this manner, a cross section of interest and a supplementary cross section as illustrated in FIG. 7A or FIG. 7B are set with respect to the fundus Ef by the user, by the cross section designator 237, or by the cooperation between the user and the cross section designator 237.

The data processor 230 that functions as described above may include, for example, a processor, a RAM, a ROM, a hard disk drive, and the like. A storage device such as a hard disk drive may store, in advance, a computer program that causes the processor to execute the above functions.

<User Interface 240>

The user interface (UI) 240 includes the display 241 and the operation device 242. The display 241 includes the display device 3 shown in FIG. 2 and/or another display device. The operation device 242 includes any types of operation devices. The user interface 240 may include, for example, a device having both a display function and an operation function, such as a touch panel.

<Data Input and Output Unit 290>

The data input and output unit 290 performs input of data into the blood flow measurement apparatus 1 and output of data from the blood flow measurement apparatus 1.

The data input and output unit 290 has, for example, a function for communicating with external devices (not shown in the figures). The data input and output unit 290 with such a communication function includes a communication interface according to the form or aspect of connection with external devices. External devices may be, for example, one or more of any type of ophthalmic apparatus. Further, External devices may be one or more of any types of information processing devices such as a hospital information system (HIS) server, a digital imaging and communications in medicine (DICOM) server, a doctor's terminal, a mobile terminal, a personal terminal, a cloud server, and other devices.

The data input and output unit 290 may include a device that reads out information from a recording medium (i.e., a data reader device), and/or a device that writes or records information into a recording medium (i.e., a data writer device), for example.

<Operation of Blood Flow Measurement Apparatus of Exemplary Embodiment>

Some examples of the operation of the blood flow measurement apparatus 1 will be described below.

It is assumed that preparatory operations such as input of patient ID, alignment, focus adjustment, and OCT optical path length adjustment have already been carried out. It is also assumed that various kinds of controls such as control for maintaining a suitable alignment state (i.e., tracking control) and control for maintaining a suitable OCT optical path length (Z lock control) have already been started. Further, it is assumed that various kinds of settings such as setting of a blood vessel of interest to which blood flow measurement (OCT scan) is to be applied and setting of a cross section of interest have already been carried out.

First Operation Example

Figure 9:
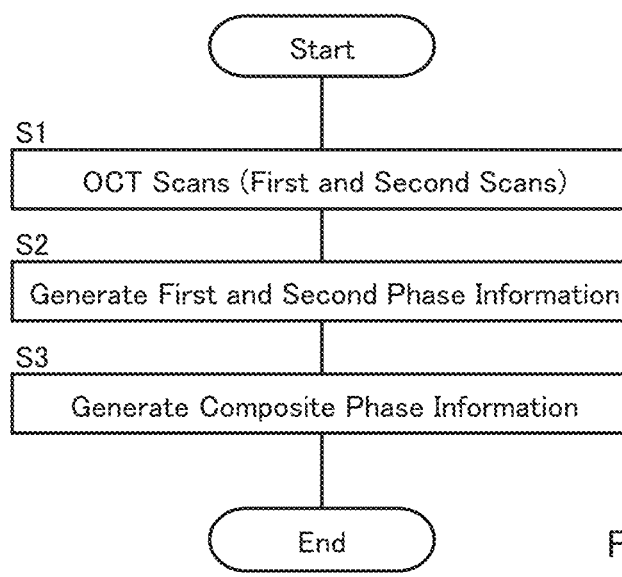
FIG. 9 is a flowchart showing an example of the operation of the blood flow measurement apparatus (optical coherence tomography apparatus) of an exemplary aspect according to the embodiment.

FIG. 9 shows the first example of the operation of the blood flow measurement apparatus 1.

(S1: OCT Scans; First and Second Scans)

First, the blood flow measurement apparatus 1 applies OCT scanning to the fundus Ef. More specifically, the main controller 211 controls the OCT unit 100, the optical scanner 44, etc. to perform at least one first scan and at least one second scan in the above-described manner that each first scan is operated to scan a cross section of the fundus Ef in the first scan direction and that each second scan is operated to scan a cross section of the fundus Ef in the second scan direction opposite to the first scan direction.

In each scan, the OCT unit 100, the optical scanner 44, etc. are controlled to perform projection of the measurement light LS, deflection of the measurement light LS, generation of the interference light LC, detection of the interference light LC, acquisition of detected data, and sampling of the detected data.

(S2: Generate First Phase Information and Second Phase Information)

The image construction unit 220 generates at least phase information based on the sampling data corresponding to each first scan performed in the step S1. The phase information generated from a first scan is referred to as first phase information. Similarly, the image construction unit 220 generates at least phase information based on the sampling data corresponding to each second scan performed in the step S1. The phase information generated from a second scan is referred to as second phase information. In the present embodiment, the first phase information is the first phase image, and the second phase information is the second phase image, as described above.

(S3: Generate Composite Phase Information)

The phase information processor 250 generates composite phase information based on the first phase information and the second phase information generated in the step S2.

The first phase information is generated from the data acquired by the first scan, and the second phase information is generated from the data acquired by the second scan. In addition, the first scan and the second scan are conducted to be performed in mutually opposite directions.

Figure 10A:
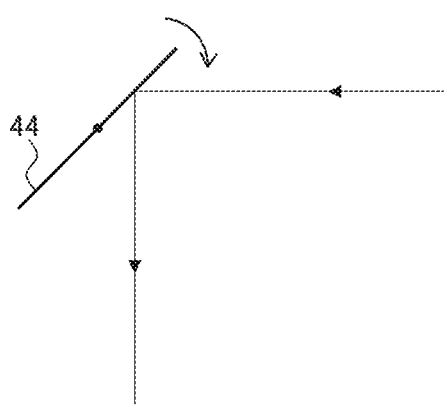
FIG. 10A is a schematic diagram for describing an example of the operation of the blood flow measurement apparatus (optical coherence tomography apparatus) of an exemplary aspect according to the embodiment.

In the event that the optical scanner 44 reflects the measurement light LS while rotating clockwise as shown in FIG. 10A, in other words, in the event that the optical scanner 44 reflects the measurement light LS while rotating so that the optical path length of the measurement light LS is getting shorter, the subject to be measured (the fundus Ef in the present embodiment) is recognized as relatively moving in a direction approaching the optical scanner 44, and an error (offset) caused by the relative movement is added to the phase information.

Figure 10B:
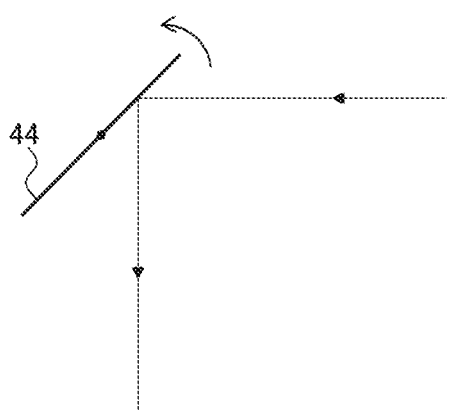
FIG. 10B is a schematic diagram for describing an example of the operation of the blood flow measurement apparatus (optical coherence tomography apparatus) of an exemplary aspect according to the embodiment.

Conversely, in the event that the optical scanner 44 reflects the measurement light LS while rotating counterclockwise as shown in FIG. 10B, in other words, in the event that the optical scanner 44 reflects the measurement light LS while rotating so that the optical path length of the measurement light LS is getting longer, the subject to be measured (the fundus Ef in the present embodiment) is recognized as relatively moving in a direction away from the optical scanner 44, and an error (offset) caused by the relative movement is added to the phase information.

Further, the optical scanner 44 such as a galvano scanner includes a reflecting mirror rotatable in a reciprocating manner. With the optical scanner 44 thus configured, a first scan is performed by the rotation in one direction (e.g., clockwise rotation), and a second scan is performed by the rotation in the opposite direction thereto (e.g., counterclockwise rotation). Such reciprocating rotations include a section (or interval) in which the reflecting mirror rotates at substantially constant speed and a section in which the reflecting mirror rotates at non-constant speed. Here, the former and the latter sections are referred to as a constant speed section and a non-constant speed section, respectively. Further, the non-constant speed section includes a section in which the rotation of the reflecting mirror accelerates from a stationary state to a constant speed state, and a section in which the rotation of the reflecting mirror decelerates from a constant speed state to a stationary state. The main controller 211 controls the OCT unit 100, the optical scanner 44, etc. to perform the OCT scanning (i.e., first and second scans) within the constant speed section.

By applying the aforementioned registration and rearrangement of A-scan image data in addition to such OCT scanning in the constant speed section, the offset (distribution of offsets) in the first phase information and the offset (distribution of offsets) in the second phase information to be composed with the first phase information may have substantially the same magnitude with each other, and the offsets may have opposite signs to each other (i.e., one of the offsets has a positive sign and the other has a negative sign). Accordingly, the offset in the first phase information may be represented by +Δφ, and the offset in the second phase information to be composed with this first phase information may be represented by −Δφ.

Therefore, averaging the first phase information and the second phase information cancels both offsets. As a result of this, the errors in phase information caused by the optical scanner 44 is canceled and eliminated.

Second Operation Example

Figure 11:
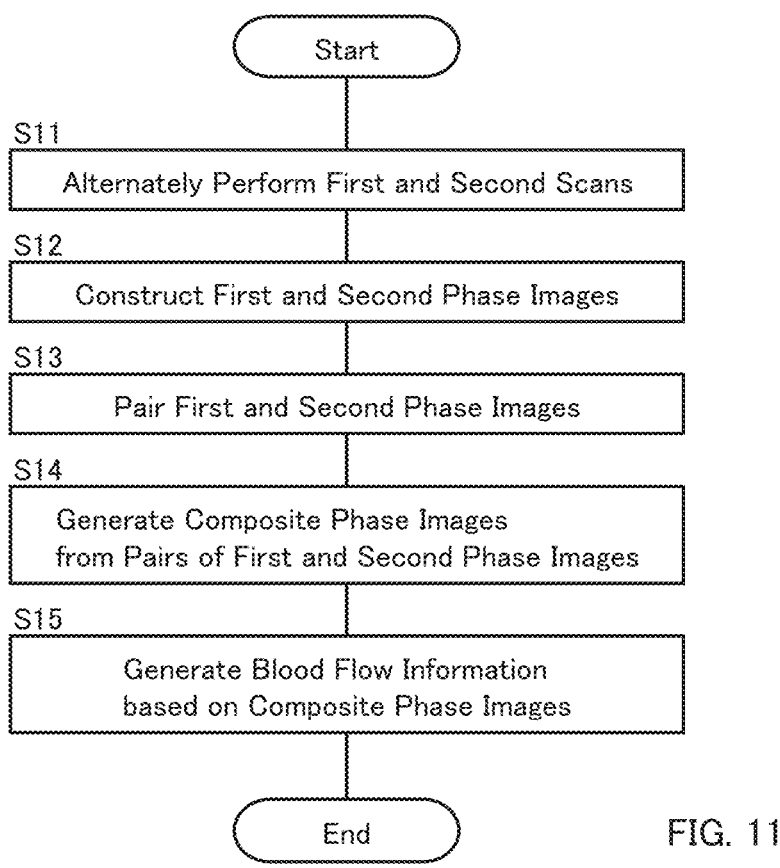
FIG. 11 is a flowchart showing an example of the operation of the blood flow measurement apparatus (optical coherence tomography apparatus) of an exemplary aspect according to the embodiment.

FIG. 11 shows the second example of the operation of the blood flow measurement apparatus 1. In the present example, the first operation example is applied to blood flow measurement.

(S11: Alternately Perform First Scan and Second Scan)

First, the blood flow measurement apparatus 1 applies OCT scanning to the fundus Ef. In the present example, the main controller 211 controls the OCT unit 100, the optical scanner 44, etc. to perform a first scan(s) and a second scan(s) in an alternate manner.

Figure 12:
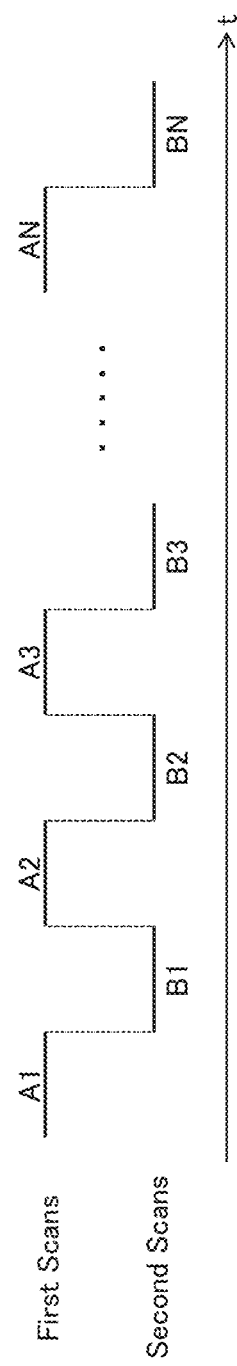
FIG. 12 is a schematic diagram for describing an example of the operation of the blood flow measurement apparatus (optical coherence tomography apparatus) of an exemplary aspect according to the embodiment.

As shown in FIG. 12, the first scan is performed N times and the second scan is also performed N times. Generally, the number N is an integer equal to or greater than 2. For example, the number N may be set to 45 in order to appropriately perform the blood flow measurement. The n-th first scan is indicated by An, and the n-th second scan is indicated by Bn (here, n=1, 2, ..., 45).

In each scan, the OCT unit 100, the optical scanner 44, and the like perform projection and deflection of the measurement light LS, generation of the interference light LC, detection of the interference light LC, and acquisition and sampling of detected data.

(S12: Construct First Phase Image and Second Phase Image)

The phase image construction unit 222 constructs a first phase image based on the sampling data corresponding to each first scan An performed in the step S11. Further, the phase image construction unit 222 constructs a second phase image based on the sampling data corresponding to each second scan Bn performed in the step S11. As a result, the number N of first phase images corresponding to the number N of first scans A1 to AN are obtained, and also the number N of second phase images corresponding to the number N of second scans B1 to BN are obtained.

(S13: Pair First Phase Image and Second Phase Image)

Figure 13:
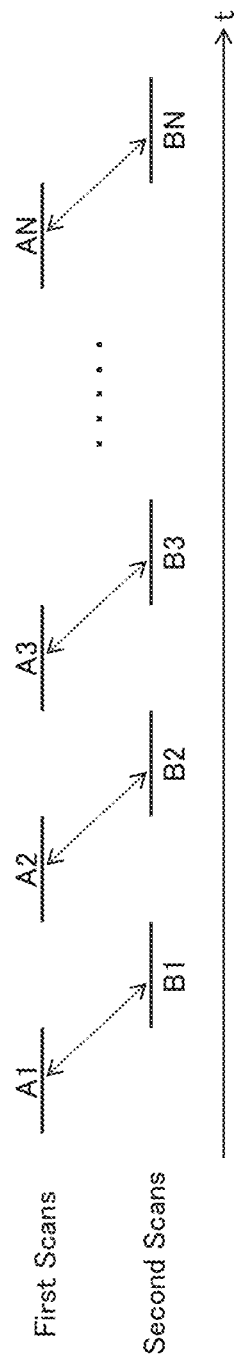
FIG. 13 is a schematic diagram for describing an example of the operation of the blood flow measurement apparatus (optical coherence tomography apparatus) of an exemplary aspect according to the embodiment.

The phase information processor 250 establishes correspondence between the number N of first phase images and the number N of second phase images acquired in the step S12. In the present example, the phase information processor 250 associates the first phase image based on the n-th first scan An and the second phase image based on the n-th second scan Bn with each other (n=1, 2, ..., N). As a result, the number N of pairs of the first phase image and the second phase image are obtained. Such pairing (or, association, correspondence) of phase images corresponds to pairing of scans shown in FIG. 13.

(S14: Generate Composite Phase Images from Pairs of First and Second Phase Images)

For each pair established in the step S13, the phase information processor 250 generates a composite phase image based on the first phase image and the second phase image of that pair. As a result, obtained are the number N of composite phase images corresponding to the number N of pairs established in the step S13.

(S15: Generate Blood Flow Information Based on Composite Phase Images)

The data processor 230 (the blood vessel region identifier 231, the blood flow information generator 232) generates blood flow information based on the number N of composite phase images obtained in the step S14. As described above, the generation of blood flow information also uses a cross sectional image based on the acquisition data obtained by any of the OCT scans performed in the step S11. Alternatively, the generation of blood flow information may also use acquisition data obtained by an OCT scan performed separately from the OCT scans in the step S11.

As described above, for each pair established in the step S13, the absolute value of the offset in the first phase image and the absolute value of the offset in the second phase image are substantially equal, and the sign of the offset in the first phase image and the sign of the offset in the second phase image are opposite to each other (i.e., one is positive and the other is negative). Therefore, both offsets may be mutually canceled by the composition of the phase images executed in the step S14. As a result, a composite phase image is obtained in which the errors caused by the optical scanner 44 have been eliminated. Accordingly, the blood flow information obtained in the step S15 can be said to be highly accurate information in which the errors caused by the optical scanner 44 have been eliminated.

Figure 14:
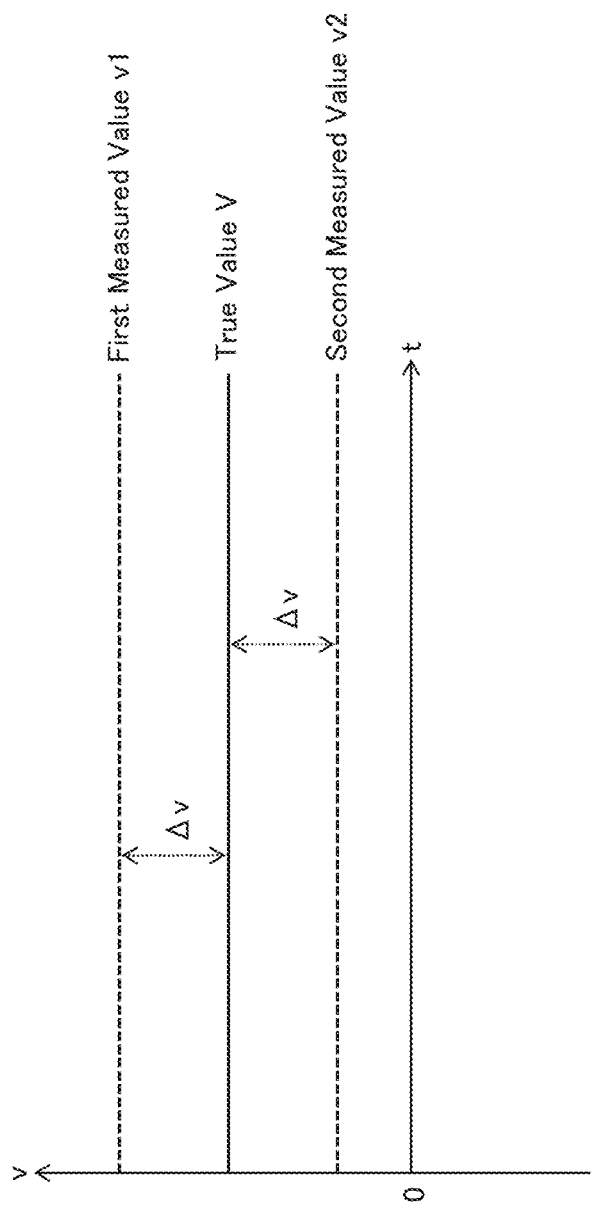
FIG. 14 is a schematic diagram for describing an example of the operation of the blood flow measurement apparatus (optical coherence tomography apparatus) of an exemplary aspect according to the embodiment.

For example, as shown in FIG. 14, when the true value of the blood flow velocity v is denoted by V, the blood flow velocity value v1 based on the first phase image (referred to as a first measured value v1) is equal to the valued obtained by adding the offset $+\Delta v$ to the true value V, and the blood flow velocity value v2 based on the second phase image (referred to as a second measured value v2) is equal to the valued obtained by adding the offset $-\Delta v$ to the true value V. That is, $v1=V+\Delta v$, $v2=V-\Delta v$. Utilizing such a composite phase image obtained by averaging the pair of the first phase image and the second phase image in blood flow velocity calculation corresponds to determining the true value V by averaging the first measured value v1 and the second measured value v2, which is represented as follows: $(v1+v2)/2=[(V+\Delta v)+(V-\Delta v)]/2=V$. The same may apply to any other blood flow parameters obtained from phase information.

<Actions and Effects of Exemplary Embodiment>

Some actions and some effects of the optical coherence tomography apparatus according to the exemplary embodiment will be described.

The optical coherence tomography apparatus of the exemplary embodiment includes a scanner, a controller, a phase information generator, and a phase information processor.

The scanner is configured to apply an OCT scan to an object using an optical scanner. As an example, the scanner of the blood flow measurement apparatus 1 includes the OCT unit 100, and the elements in the fundus camera unit 2 that form a measurement arm, and applies OCT scanning to the subject's eye E (the fundus Ef) using the optical scanner 44.

The controller is configured to control the scanner to perform at least one first scan that scans a cross section of the object in a first scan direction, and at least one second scan that scans a cross section of the object in a second scan direction opposite to the first scan direction. As an example, the controller of the blood flow measurement apparatus 1 includes a processor (the main controller 211) that operates according to software for scan control, and controls the OCT unit 100 and the optical scanner 44 so that at least one first scan and at least one second scan are applied to the fundus Ef.

The phase information generator is configured to generate at least one piece of first phase information based on at least one piece of first acquisition data acquired by the at least one first scan, and also generate at least one piece of second phase information based on at least one piece of second acquisition data acquired by the at least one second scan. As an example, the phase information generator of the blood flow measurement apparatus 1 includes the phase image construction unit 222, and generates at least one piece of first phase information (at least one piece of first phase image) and at least one piece of second phase information (at least one piece of second phase image).

The phase information processor is configured to generate composite phase information based on the at least one piece of first phase information and the at least one piece of second phase information. As an example, the phase information processor of the blood flow measurement apparatus 1 includes the phase information processor 250, and generates composite phase information (composite phase image) based on the at least one first phase image and the at least one second phase image.

According to the optical coherence tomography apparatus configured as above, phase offsets caused by the optical scanner can be canceled by composing the first phase information and the second phase information obtained by the first scan and the second scan that are performed in the opposite directions to each other. This makes it possible to eliminate the errors in phase information caused by the optical scanner.

The mode of OCT scanning (the mode of controlling OCT scanning) may be arbitrary. For example, the controller may be configured to control the scanner to perform one or more first scans and one or more second scans in an alternate manner. Further, the controller may be configured to control the scanner to perform a single first scan and a single second scan in an alternate manner (see FIG. 6C).

Further, the controller may be configured to control the scanner to apply, to a same cross section, a single first scan and a single second scan in an alternate manner. As an example, the controller of the blood flow measurement apparatus 1 may be configured to apply a single first scan and a single second scan in an alternate manner, to the cross section of interest CS or C0.

When a first scan and a second scan are applied in an alternate manner (to a single cross section or two or more cross sections), the phase information processor may generate composite phase information based on first phase information corresponding to one first scan and also on second phase information corresponding to a second scan performed immediately before or immediately after that first scan.

With such a configuration, composite phase information may be generated from a first phase information and a second phase information obtained based respectively on a first scan and a second scan performed with an extremely short time lag between them. Therefore, for example, when measuring hemodynamics, the errors in phase information caused by the optical scanner may be preferably eliminated by composing the first phase information and the second phase information of substantially the same time phase.

In the case where a first scan and a second scan are performed in an alternate manner, or in the case where a first scan and a second scan are not performed in an alternate manner, the phase information processor may generate composite phase information, based on first phase information corresponding to one first scan and also on second phase information corresponding to a second scan where a time lag (e.g., a difference in execution timing or a difference in execution order) between the first scan and the second scan is not exceeding a predetermined threshold.

According to such a configuration, the composite phase information can be generated from the first phase information and the second phase information obtained based respectively on the first scan and the second scan performed with a short time lag between them. Therefore, the errors in phase information caused by the optical scanner may be preferably eliminated in hemodynamics measurements.

There may be cases of handling phase information that represents a substantially periodic change (variation, movement, motion, etc.) of an object, such as blood flow parameters. In such cases, the phase information processor may be configured to generate composite phase information, based on first phase information corresponding to one first scan performed at one time phase in the substantially periodic change of the object, and also on second phase information corresponds to a second scan performed at a time phase substantially the same as the time phase for that first scan.

With such a configuration, the phase information processor can select and compose the first phase information and the second phase information corresponding to substantially the same time phase. Therefore, the errors in phase information caused by the optical scanner may be appropriately eliminated.

The phase information processor may be configured to generate composite phase information by averaging first phase information and second phase information. Note that the calculation of composing phase information is not limited to averaging.

The optical scanner like a galvano scanner includes a reflecting mirror(s) rotatable in a reciprocating manner. If this is the case, the controller may control the scanner to acquire data while the reflecting mirror is rotating at substantially a constant speed.

According to such a configuration, the absolute value of the offset in the first phase information and the absolute value of the offset in the second phase information can be made substantially equal to each other. In addition, the signs (positive or negative) of these offsets can be made opposite to each other according to this configuration. As a result, it becomes possible to facilitate the calculation of composing phase information for canceling the offsets. For example, the offsets can be compensated by a simple average calculation.

Note that it may be adopt a configuration of performing data acquire data (i.e., OCT scanning) while the reflecting mirror is rotating at a non-constant speed as well. In this case, more complicated processing is required than the above case, but values related to non-constant rotation speed (theoretical value, specification value, measured value, etc.) can be derived.

The controller may be configured to control the scanner to repeatedly perform each of a first scan and a second scan. In other words, the controller may be configured to perform a plurality of scans consisting of both a plurality of first scans and a plurality of second scans, in any order. If this is the case, the phase information generator may generate a plurality of pieces of first phase information obtained based respectively on a plurality of pieces of first acquisition data acquired respectively by the plurality of first scans, and also generate a plurality of pieces of second phase information obtained based respectively on a plurality of pieces of second acquisition data acquired respectively by the plurality of second scans. Based on the plurality of pieces of first phase information and the plurality of pieces of second phase information, the phase information processor may then generate a plurality of phase information groups each of which includes both one or more pieces of first phase information and one or more pieces of second phase information. In addition, the phase information processor may generate a plurality of pieces of composite phase information based respectively on the plurality of phase information groups.

As an example, the blood flow measurement apparatus 1 may perform the N times of the first scan An, and also perform the N times of the second scan Bn. Then, the blood flow measurement apparatus 1 may generate the number N of first phase images corresponding to the N times of the first scan An, and also generate the number N of second phase images corresponding to the N times of the second scan Bn. Further, the blood flow measurement apparatus 1 may construct the N number of phase information groups (e.g., the N number of pairs of phase images) by executing paring between the number N of first phase images and the number N of second phase images. Finally, the blood flow measurement apparatus 1 may generate the number N of pieces of composite phase information (e.g., the number N of composite phase images) based respectively on the number N of phase image pairs. As a result of such processes, the number N of composite phase images are obtained as time series data.

Such a configuration is capable of yielding time series composite phase information in which the errors in phase information caused by the optical scanner have been eliminated. From such time series composite phase information, it is possible to obtain data in which phase information changes in time series, with high accuracy.

For example, the blood flow measurement apparatus 1 may generate blood flow information representing hemodynamics of a living body, based on the plurality of pieces of composite phase information, for example, based on the N number of time series composite phase images. The generation of the blood flow information may be carried out by the data processor 230 that includes the blood flow information generator 232.

Some exemplary embodiments provide a method of controlling an optical coherence tomography apparatus. The optical coherence tomography apparatus to which the control method may be applied includes a processor and a scanner configured to apply an OCT scan to an object using an optical scanner. The control method includes at least the following steps: controlling the scanner to perform at least one first scan that scans a cross section of the object in a first scan direction; controlling the scanner to perform at least one second scan that scans a cross section of the object in a second scan direction opposite to the first scan direction; controlling the processor to generate at least one piece of first phase information based on at least one piece of first acquisition data acquired by the at least one first scan; controlling the processor to generate at least one piece of second phase information based on at least one piece of second acquisition data acquired by the at least one second scan; and controlling the processor to generate composite phase information based on the at least one piece of first phase information and the at least one piece of second phase information.

Any of the matters, items, elements, or the like described in the exemplary embodiment may be combined with such a control method of the optical coherence tomography apparatus.

The exemplary embodiment provides a program that causes a computer to perform the control method described above. Any of the matters, items, elements, or the like described in the exemplary embodiment may be combined with such a program.

Further, a computer-readable non-transitory recording medium storing such a program may be created. Any of the matters, items, elements, or the like described in the exemplary embodiment may be combined with such a recording medium. The non-transitory recording medium may be in any form, and examples thereof include a magnetic disk, an optical disk, a magneto-optical disk, a semiconductor memory, and the like.

Some exemplary embodiments provide an optical measurement method. The optical measurement method acquires data by applying OCT scanning to an object using an optical scanner. In addition, the optical measurement method includes at least the following steps: performing at least one first scan that scans a cross section of the object in a first scan direction; performing at least one second scan that scans a cross section of the object in a second scan direction opposite to the first scan direction; generating at least one piece of first phase information based on at least one piece of first acquisition data acquired by the at least one first scan; generating at least one piece of second phase information based on at least one piece of second acquisition data acquired by the at least one second scan; and generating composite phase information based on the at least one piece of first phase information and the at least one piece of second phase information.

Any of the matters, items, elements, or the like described in the exemplary embodiment may be combined with such an optical measurement method.

The exemplary embodiment provides a program that causes an optical coherence tomography apparatus to perform such an optical measurement method. Any of the matters, items, elements, or the like described in the exemplary embodiment may be combined with such a program.

Further, a computer-readable non-transitory recording medium storing such a program may be created. Any of the matters, items, elements, or the like described in the exemplary embodiment may be combined with such a recording medium. The non-transitory recording medium may be in any form, and examples thereof include a magnetic disk, an optical disk, a magneto-optical disk, a semiconductor memory, and the like.

With the control method, the optical measurement method, the program, or the recording medium according to the exemplary embodiment, the errors in phase information caused by the optical scanner may be eliminated. In addition, achieved are actions and effects corresponding to matters, items, elements, or the like combined with the control method, the optical measurement method, the program, or the recording medium according to the exemplary embodiment.

The embodiments described above are merely illustrative aspects of the implementation of the present invention. Therefore, any modifications (e.g., omission, substitution, replacement, addition, etc.) may be made within the scope of the present invention.

For example, any of the aspects described in the embodiments may be applied to a modality apparatus of a type different from the optical coherence tomography apparatus which suffers from an error of phase information caused by an optical scanner.

The example embodiment described above is configured for removing the offsets caused by the movement of the subject to be measured, by considering the average of the data obtained by the reciprocating scans or the like. More specifically, given that the true value of the flow velocity is denoted by V and the offset is denoted by $\Delta v$, the measurement results obtained from two scans in mutually opposite directions are a combination of V+$\Delta v$ and V−$\Delta v$. Then, taking the average of the two measurement results, the offset $\Delta v$ is eliminated and the true value V is derived as follows: [(V+$\Delta v$)+(V−$\Delta v$)]/2=V.

On the other hand, if the difference between the two measurement results is divided by 2, that is, if the difference average is taken, the offset $\Delta v$ may be calculated as follows: [(V+$\Delta v$)−(V−$\Delta v$)]/2=$\Delta v$. By using this relationship, it is possible to eliminate the measurement error caused by the offset without having to perform reciprocating scans or the like.

For that purpose, for example, a sample that has a known flow velocity may be prepared. This sample may be an instrument for offset calibration. Such a specially designed object is referred to as a phantom. The offset amount $\Delta v$ for an OCT apparatus may be derived by, for example, applying reciprocating scans or the like to the phantom to obtain a measurement result of flow velocity, and then performing a calculation using the flow velocity measurement result and the relational expression described above.

The calculated offset amount $\Delta v$ is stored in the OCT apparatus itself or in a storage device accessible by the OCT apparatus. By correcting a measurement result of flow velocity obtained from actual OCT scanning with the OCT apparatus by using the offset amount $\Delta v$, the error included in this flow velocity measurement result may be eliminated.

According to such a method or technique, an error inevitably mixed in a measurement result is expected to be eliminated even if the mode of OCT scanning applied to the actual subject to be measured is not reciprocating scanning or the like but a normal type of scanning such as unidirectional scanning.

It should be noted that offset calibration does not need to be carried out using a phantom. In some examples, offset calibration may be carried out as a preliminary measurement for actual measurements of a subject. In some other examples, offset calibration may be carried out using a sample different from both a phantom and an actual subject to be measured.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. An optical coherence tomography (OCT) apparatus comprising:
   a scanner configured to apply an OCT scan with a measurement light to an object using an optical scanner;
   a controller circuit configured to control the scanner to perform at least one first scan that scans a first cross section of the object in a first scan direction and at least one second scan that scans a second cross section of the object in a second scan direction opposite to the first scan direction;
   a phase information generator circuit configured to generate at least one piece of first phase information based on at least one piece of first acquisition data acquired by the at least one first scan and at least one piece of second phase information based on at least one piece of second acquisition data acquired by the at least one second scan; and
   a phase information processor circuit configured to generate composite phase information based on the at least one piece of first phase information and the at least one piece of second phase information, wherein
   the scanner includes a reflecting mirror configured to rotate about an axis,
   the measurement light is reflected at a position off the axis of the reflecting mirror, and
   the phase information processor circuit is further configured to eliminate an error in the generated composite phase information caused by the measurement light being reflected at the position off the axis of the reflecting mirror.

2. The OCT apparatus of claim 1, wherein the controller circuit is configured to control the scanner to perform one or more first scans of the at least one first scan and one or more second scans of the at least one second scan in an alternate manner.

3. The OCT apparatus of claim 2, wherein the controller circuit is configured to control the scanner to perform a single first scan of the one or more first scans and a single second scan of the one or more second scans in an alternate manner.

4. The OCT apparatus of claim 3, wherein the first cross section and the second cross section are a same cross section, and the controller circuit is configured to control the scanner to apply the single first scan of the one or more first scans and the single second scan of the one or more second scans in an alternate manner to the same cross section.

5. The OCT apparatus of claim 4, wherein the phase information processor circuit is configured to generate the composite phase information based on first phase information corresponding to a first scan of the at least one first scan and second phase information corresponding to a second scan of the at least one second scan performed immediately before or immediately after the first scan,
wherein the first phase information corresponding to the first scan is one of the at least one piece of first phase information, and the second phase information corresponding to the second scan is one of the at least one piece of second phase information.

6. The OCT apparatus of claim 3, wherein the phase information processor circuit is configured to generate the composite phase information based on first phase information corresponding to a first scan of the at least one first scan and second phase information corresponding to a second scan of the at least one second scan performed immediately before or immediately after the first scan,
wherein the first phase information corresponding to the first scan is one of the at least one piece of first phase information, and the second phase information corresponding to the second scan is one of the at least one piece of second phase information.

7. The OCT apparatus of claim 2, wherein the phase information processor circuit is configured to generate the composite phase information based on first phase information corresponding to a first scan of the at least one first scan and second phase information corresponding to a second scan of the at least one second scan where a time lag between the first scan and the second scan is not exceeding a predetermined threshold,
wherein the first phase information corresponding to the first scan is one of the at least one piece of first phase information, and the second phase information corresponding to the second scan is one of the at least one piece of second phase information.

8. The OCT apparatus of claim 2, wherein
the phase information represents a substantially periodic change of the object, and
the phase information processor circuit is configured to generate the composite phase information based on first phase information corresponding to a first scan of the at least one first scan performed at a first time phase of the change and second phase information corresponding to a second scan of the at least one second scan performed at a second time phase, wherein
the first phase information corresponding to the first scan is one of the at least one piece of first phase information, and the second phase information corresponding to the second scan is one of the at least one piece of second phase information, and
the first time phase and the second time phase include a same periodic change.

9. The OCT apparatus of claim 2, wherein
the reflecting mirror is configured to be rotatable in a reciprocating manner, and
the controller circuit is configured to control the scanner to acquire data while the reflecting mirror is rotating at substantially a constant speed.

10. The OCT apparatus of claim 1, wherein the phase information processor circuit is configured to generate the composite phase information based on first phase information corresponding to a first scan of the at least one first scan and second phase information corresponding to a second scan of the at least one second scan where a time lag between the first scan and the second scan is not exceeding a predetermined threshold,
wherein the first phase information corresponding to the first scan is one of the at least one piece of first phase information, and the second phase information corresponding to the second scan is one of the at least one piece of second phase information.

11. The OCT apparatus of claim 1, wherein
the phase information represents a substantially periodic change of the object, and
the phase information processor circuit is configured to generate the composite phase information based on first phase information corresponding to a first scan of the at least one first scan performed at a first time phase of the change and second phase information corresponding to a second scan of the at least one second scan performed at a second time phase, wherein
the first phase information corresponding to the first scan is one of the at least one piece of first phase information, and the second phase information corresponding to the second scan is one of the at least one piece of second phase information, and
the first time phase and the second time phase include a same periodic change.

12. The OCT apparatus of claim 1, wherein the phase information processor circuit is configured to generate the composite phase information by averaging the at least one piece of first phase information and the at least one piece of second phase information.

13. The OCT apparatus of claim 1, wherein
the reflecting mirror is configured to be rotatable in a reciprocating manner, and
the controller circuit is configured to control the scanner to acquire data while the reflecting mirror is rotating at substantially a constant speed.

14. The OCT apparatus of claim 1, wherein
the phase information generator circuit includes a phase image construction unit configured to construct a phase image that represents a temporal change in a phase difference, and
the phase information processor circuit is configured to generate the composite phase information based on at least one first phase image corresponding to the at least one first scan and at least one second phase image corresponding to the at least one second scan.

15. The OCT apparatus of claim 1, wherein
the controller circuit is configured to control the scanner to repeatedly perform each of the at least one first scan and the at least one second scan, thereby performing a plurality of first scans to acquire a plurality of pieces of first acquisition data and a plurality of second scans to acquire a plurality of pieces of second acquisition data, the phase information generator circuit is configured to generate a plurality of pieces of first phase information based on the plurality of pieces of first acquisition data, and to generate a plurality of pieces of second phase information based on the plurality of pieces of second acquisition data, and the phase information processor circuit is configured to generate a plurality of phase information groups each of which includes both one or more pieces of first phase information and one or more pieces of second phase information based on the plurality of pieces of first phase information and the plurality of pieces of second phase information, and to generate a plurality of pieces of composite phase information based respectively on the plurality of phase information groups, wherein the plurality of pieces of composite phase information includes the composite phase information generated based on the at least one piece of first phase information and the at least one piece of second phase information.

16. The OCT apparatus of claim 15, wherein the object is a living body, and the OCT apparatus further comprising a blood flow information generator circuit configured to generate blood flow information representing hemodynamics of the living body based on the plurality of pieces of composite phase information generated from the plurality of phase information groups by the phase information processor circuit.

17. A method of controlling an optical coherence tomography (OCT) apparatus that includes a processor circuit and a scanner configured to apply an OCT scan with a measurement light to an object using an optical scanner, the method comprising:

controlling the scanner to perform at least one first scan that scans a cross section of the object in a first scan direction;

controlling the scanner to perform at least one second scan that scans the cross section of the object in a second scan direction opposite to the first scan direction;

controlling the processor circuit to generate at least one piece of first phase information based on at least one piece of first acquisition data acquired by the at least one first scan;

controlling the processor circuit to generate at least one piece of second phase information based on at least one piece of second acquisition data acquired by the at least one second scan; and controlling the processor circuit to generate composite phase information based on the at least one piece of first phase information and the at least one piece of second phase information, wherein the scanner includes a reflecting mirror configured to rotate about an axis, the measurement light is reflected at a position off the axis of the reflecting mirror, and the controlling the processor circuit to generate the composite phase information includes eliminating an error in the generated composite phase information caused by the measurement light being reflected at the position off the axis of the reflecting mirror.

18. A computer-readable non-transitory recording medium storing a program configured to cause a computer to execute the method of controlling the OCT apparatus of claim 17.

19. An optical measurement method for acquiring data by applying an optical coherence tomography (OCT) scan with a measurement light to an object using an optical scanner, the method comprising:

performing at least one first scan that scans a cross section of the object in a first scan direction;

performing at least one second scan that scans the cross section of the object in a second scan direction opposite to the first scan direction;

generating at least one piece of first phase information based on at least one piece of first acquisition data acquired by the at least one first scan;

generating at least one piece of second phase information based on at least one piece of second acquisition data acquired by the at least one second scan; and generating composite phase information based on the at least one piece of first phase information and the at least one piece of second phase information wherein the scanner includes a reflecting mirror configured to rotate about an axis, the measurement light is reflected at a position off the axis of the reflecting mirror, and the generating the composite phase information includes eliminating an error in the generated composite phase information caused by the measurement light being reflected at the position off the axis of the reflecting mirror.

20. A computer-readable non-transitory recording medium storing a program configured to cause an optical coherence tomography (OCT) apparatus to execute the optical measurement method of claim 19.

* * * * *